US009487754B2

(12) United States Patent
Mao et al.

(10) Patent No.: US 9,487,754 B2
(45) Date of Patent: Nov. 8, 2016

(54) DERIVATION OF FIBROCHONDROCYTES FROM PROGENITOR CELLS

(75) Inventors: Jeremy J. Mao, Closter, NJ (US); Chang Hun Lee, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 245 days.

(21) Appl. No.: 13/877,260

(22) PCT Filed: Oct. 3, 2011

(86) PCT No.: PCT/US2011/054660
§ 371 (c)(1),
(2), (4) Date: Nov. 8, 2013

(87) PCT Pub. No.: WO2012/045094
PCT Pub. Date: Apr. 5, 2012

(65) Prior Publication Data
US 2014/0079739 A1    Mar. 20, 2014

Related U.S. Application Data

(60) Provisional application No. 61/388,791, filed on Oct. 1, 2010.

(51) Int. Cl.
*C12N 5/00* (2006.01)
*A61K 38/18* (2006.01)
*C12N 5/077* (2010.01)

(52) U.S. Cl.
CPC ............. *C12N 5/0655* (2013.01); *A61K 38/18* (2013.01); *A61L 2430/06* (2013.01); *C12N 2501/10* (2013.01); *C12N 2501/15* (2013.01); *C12N 2531/00* (2013.01); *C12N 2533/40* (2013.01)

(58) Field of Classification Search
CPC ............ C12N 5/0655; C12N 2501/10; C12N 2533/40; C12N 2501/15; C12N 2531/00; A61L 2430/06; A61L 2430/24; A61K 38/18
USPC .......................... 514/8.9; 435/366, 405, 377
See application file for complete search history.

(56) References Cited

U.S. PATENT DOCUMENTS

| | | | | |
|---|---|---|---|---|
| 6,464,983 | B1* | 10/2002 | Grotendorst | 424/198.1 |
| 2003/0040113 | A1 | 2/2003 | Mizuno et al. | |
| 2004/0010320 | A1* | 1/2004 | Huckle | A61L 27/38 623/23.72 |
| 2010/0034892 | A1 | 2/2010 | Mao | |

FOREIGN PATENT DOCUMENTS

| | | |
|---|---|---|
| WO | WO 2006/064025 | 6/2006 |
| WO | WO 2008/100534 | 8/2008 |
| WO | WO 2009/149093 | 12/2009 |

OTHER PUBLICATIONS

Moioli et al., Sustained release of TGFβ3 from PLGA microspheres and its effect on early osteogenic differentiation of human mesenchymal stem cells. Tissue Engineering, vol. 12, No. 3 (2006) pp. 537-546.*
Jaklenec et al., Sequential release of bioactive IGF-1 and TGF-β1 from PLGA microsphere-based scaffolds. Biomaterials, vol. 29 (2008) pp. 1518-1525.*
Seyedin et al., In vitro induction of cartilage-specific macromolecules by a bone extract. Journal of Cell Biology, vol. 97 (Dec. 1983) pp. 1950-1953.*
Centeno et al., Regeneration of meniscus cartilage in a knee treated with percutaneously implanted autologous mesenchymal stem cells. Medical Hypotheses, vol. 71, No. 6 (Dec. 2008) pp. 900-908.*
Alpaslan et al., Long-term evaluation of recombinant human bone morphogenetic protein-2 induced bone formation with a biologic and synthetic delivery system, Br J of Oral Maxillofac Surg., 1996, pp. 414-418, vol. 34.
Bax et al., Bone Morphogenetic Protein-2 Increases the Rate of Callus Formation after Fracture of the Rabbit Tibia, Calcif Tissue Int., 1999, pp. 83-89, vol. 65.
Connelly et al., Tensile Loading Modulates Bone Marrow Stromal Cell Differentiation and the Development of Engineered Fibrocartilage Constructs, 2010, pp. 1913-1923, vol. 16, No. 6.
DePuy Spine, downloaded from the internet at www.depuy.com/about-depuy/depuy-divisions/depuy-spine on Aug. 25, 2014, 1 page.
Dillon et al., RNAi as an Experimental and Therapeutic Tool to Study and Regulate Physiological and Disease Processes, Annu Rev Physiol., 2005, pp. 147-173, vol. 67.
Dutton et al., Enhancement of meniscal repair in the avascular zone using mesenchymal stem cells in a porvine model, J Bone & Joint Surgery, 2010, pp. 169-175, vol. 92-B, No. 1.
Dykxhoorn et al., The Silent Revolution: RNA Interference as Basic Biology, Research Tool, and Therapeutic, Annu Rev Med., 2005, pp. 401-423, vol. 56.
Elhai et al., Conjugal Transfer of DNA to Cyanobacteria, Methods in Enzymology, 1988, pp. 747-754, vol. 167.
Ghadessy et al., Directed evolution of polymerase function by compartmentalized self-replication, PNAS, 2001, pp. 4552-4557, vol. 98, No. 8.
Helene et al., Control of Gene Expression by Triple Helix-Forming Oligonucleotides, Ann. NY. Acad. Sci., 1992, pp. 27-36, vol. 660.
International Search Report and Written Opinion in corresponding International Application No. PCT/US2011/054660 dated Jan. 26, 2012, 7 pages.

(Continued)

*Primary Examiner* — Kara Johnson
(74) *Attorney, Agent, or Firm* — Dentons US LLP

(57) ABSTRACT

Provided herein are compositions and methods for forming fibrochondrocytes or fibrochondrocyte-like cells from progenitor cells, such as mesenchymal stem cells. One aspect provides a fibrochondrocyte culture medium including CTGF and TGFβ3, optionally encapsulated by microspheres having different release profiles. Another aspect provides a method for forming fibrochondrocytes or fibrochondrocyte-like cells from progenitor cells by culturing with CTGF and TGFβ3.

14 Claims, 22 Drawing Sheets

(56) References Cited

OTHER PUBLICATIONS

Isobe et al., Bone Regeneration Produced in Rat Femur Defects by Polymer Capsules Containing Recombinant Human Bone Morphogenetic Protein-2, J Oral Maxillofac Surg., 1999, pp. 695-698, vol. 57.
ISTO Technologies, Inc., downloaded on from the internet at www.istotech.com/products.html on Aug. 25, 2014, 1 page.
Kuboki et al., Two Distinctive BMP-Carriers Induce Zonal Chondrogenesis and Membranous Ossification, Respectively; Geometrical Factors of Matrices for Cell-Differentiation, Connective Tissue Res., 1995, pp. 219-226, vol. 32. Nos. 1-4.
Lee et al., Aptamer therapeutics advance, Curr. Opinion Chem. Biol., 2006, pp. 282-289, vol. 10.
Lee et al., CTGF directs fibroblast differentiation from human mesenchymal stem/stromal cells and defines connective tissue healing in a rodent injury model, J Clin Invest., 2010, pp. 3340-3349, vol. 120, No. 9.
Link et al., Beyond toothpicks: new methods for isolation mutant bacteria, Nature Reviews, 2007, pp. 680-688, vol. 5, No. 9.
Maher, DNA Triple-Helix Formation: An Approach to Artificial Gene Repressors?, BioEssays, 1992, pp. 807-815, vol. 14, No. 12.
Marion et al., Mesenchymal Stem Cells and Tissue Engineering, Methods in Enzymology, 2006, pp. 339-361, vol. 420.
Murata et al., Carrier-dependency of cellular differentiation induced by bone morphogenetic protein in ectopic sites, Int. J. Oral Maxillofac. Surg., 1998, pp. 391-396, vol. 27.
Orthofix, downloaded from the internet at www.orthofix.com/products/trinity-evolution.asp?cid=36 on Aug. 25, 2014, 2 pages.
Osiris, downloaded from the internet at www.osiris.com/biosurgery_osteo.php on Aug. 25, 2014, 1 page.
Pushparaj et al., Frontiers in Research Review: Cutting Edge Molecular Approaches to Therapeutics Short Interfering RNA (siRNA) as a Novel Therapeutic, Clinical and Experimental Pharmacology and Physiology, 2006, pp. 504-510, vol. 33.
Reynolds et al., Rational siRNA design for RNA interference, Nature Biotechnology, 2004, pp. 326-330, vol. 22, No. 3.
Sagner et al., Rapid filter assay for the detection of DNA polymerase activity: direct identification of the gene for the DNA polymerase from *Thermus aquaticus*, Gene, 1991, pp. 119-123, vol. 97, No. 1.
Saito et al., New synthetic biodegradable polymers as BMP carriers for bone tissue engineering, Biomaterials, 2003, pp. 2287-2293, vol. 24.
Santos et al., Si—Ca—P xerogels and bone morphogenetic protein act synergistically on a rat stromal marrow cell differentiation in vitro, J Biomed Mater Res., 1998, pp. 87-94, vol. 41.
Spinalrestoration, downloaded from the internet at www.spinalrestoration.com/products/index.html on Aug. 26, 2014, 1 page.
Stryker, downloaded from the internet at http://www.stryker.com/en-us/products/Orthobiologicals/index.htm on Aug. 25, 2014, 1 page.
Studier, Protein production by auto-induction in high-density shaking cultures, Protein Expression Purification, 2005, pp. 207-234, vol. 41.
Sweeney et al., Repair of critical size rat calvarial defects using extracellular matrix protein gels, J Neurosurg, 1995, pp. 710-715, vol. 83.
Tuli et al., Transforming Growth Factor-Beta-Mediated Chondrogenesis of Human Mesenchymal Progenitor Cells Involves N-cadherin and Mitogen-activated Protein Kinase and Wnt Signaling Cross-talk, J. Biol. Chem., 2003, pp. 41227-41236, vol. 278, No. 42.
Viljanen et al., Low dosage of native allogeneic bone morphogenetic protein in repair of sheep calvarial defects, Int. J. Oral Maxillofac. Surg., 1997, pp. 389-393, vol. 26.
Yang et al., Clones of Ectopic Stem Cells in the Regeneration of Muscle Defects In Vivo, PloS ONE, 2010, pp. 1-8, e13547, vol. 5, No. 10.
Geron, Investor Relations, dated 2010, downloaded at http://ir.geron.com/phoenix.zhtml?c=67323&p=irol-newsArticle&Id=1636144&highlight= on Aug. 25, 2014, 3 pages.

\* cited by examiner

FIG. 8B-C
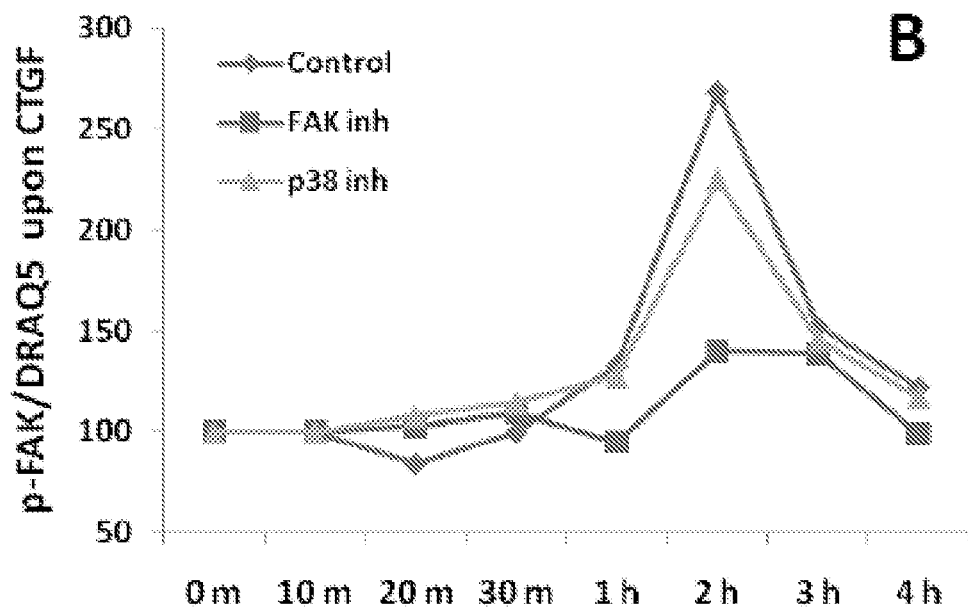
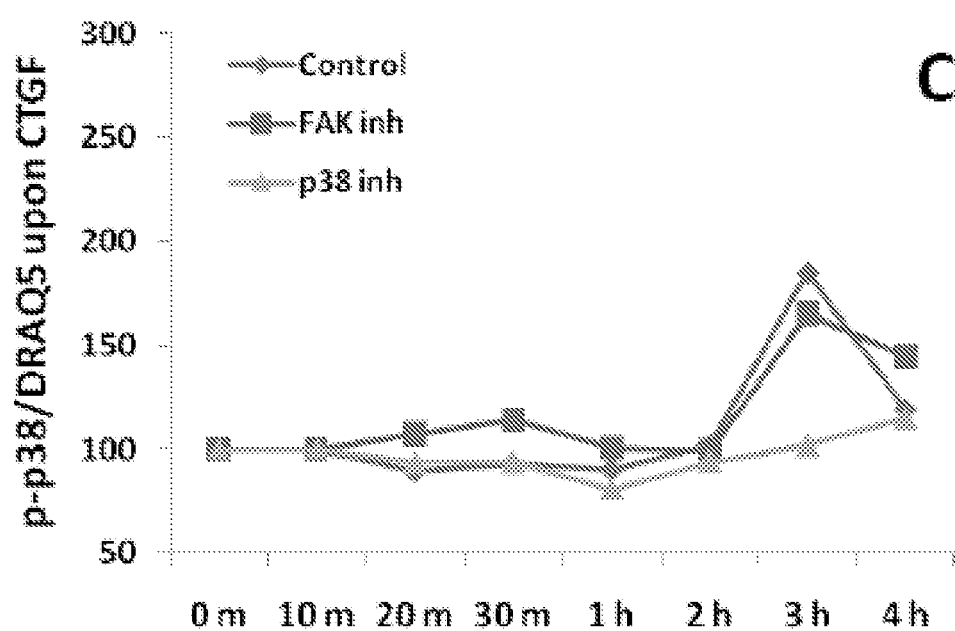

FIG. 9B-C
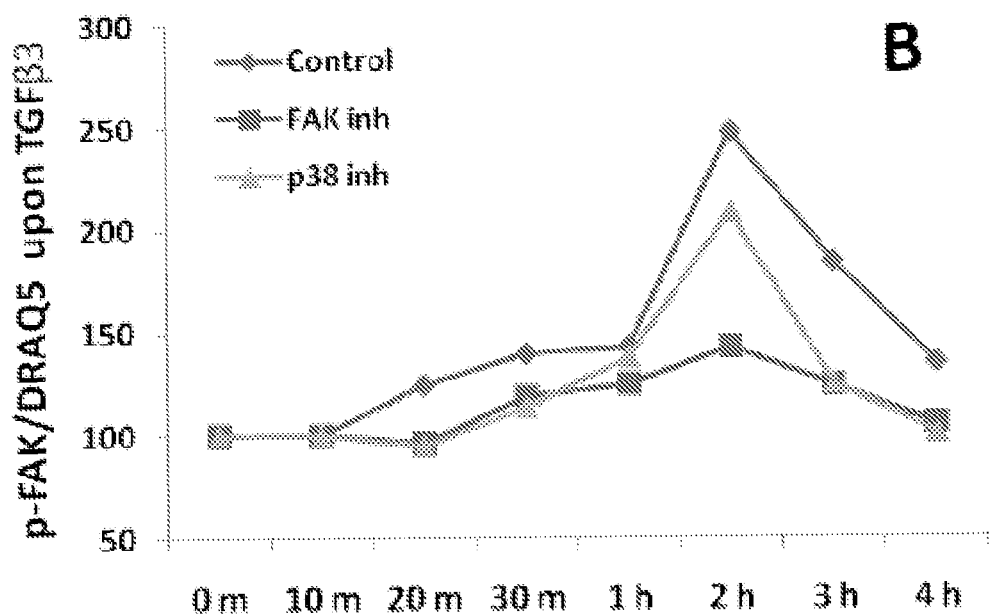
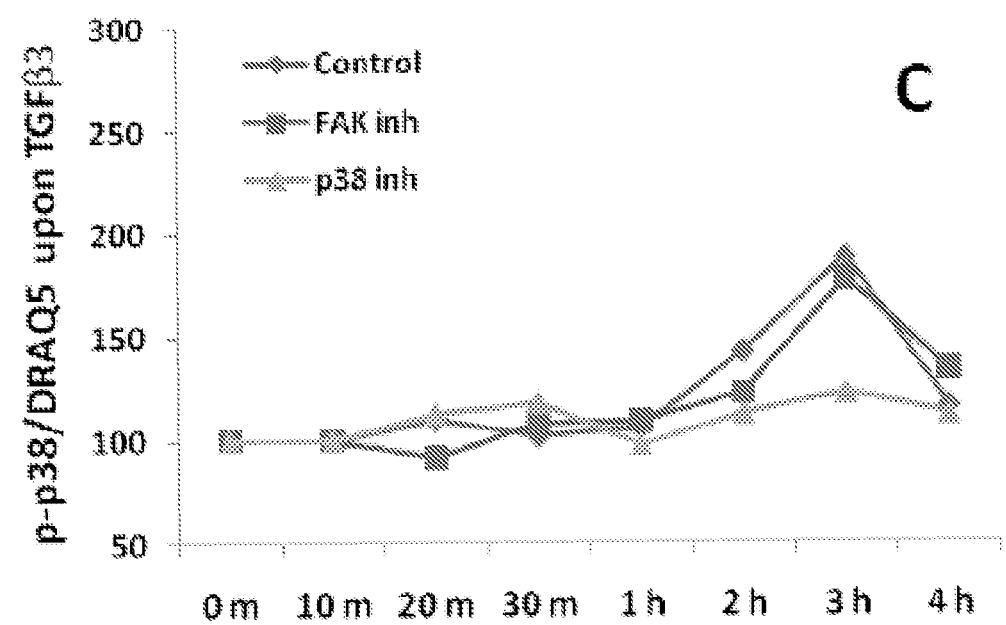

FIG. 13
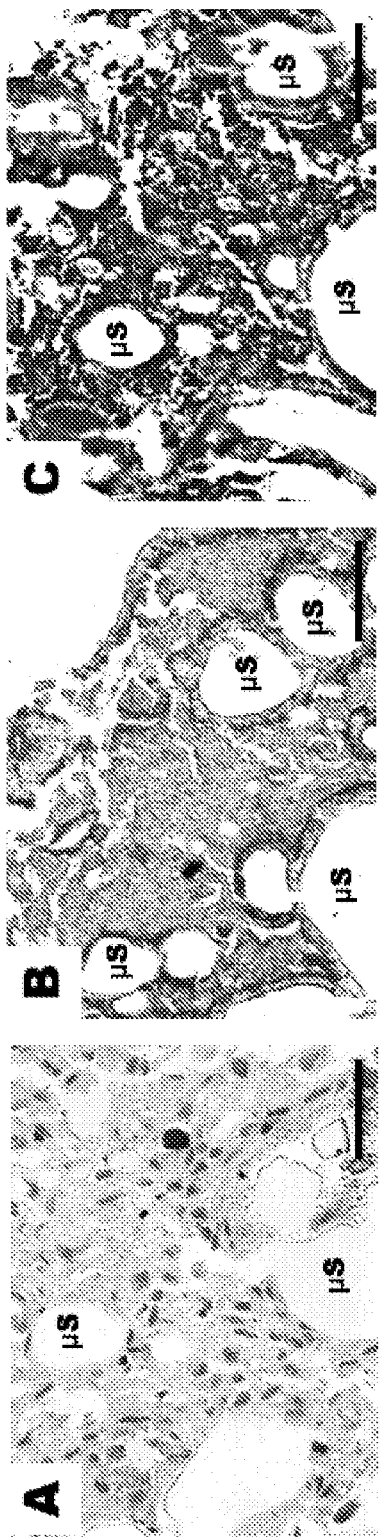
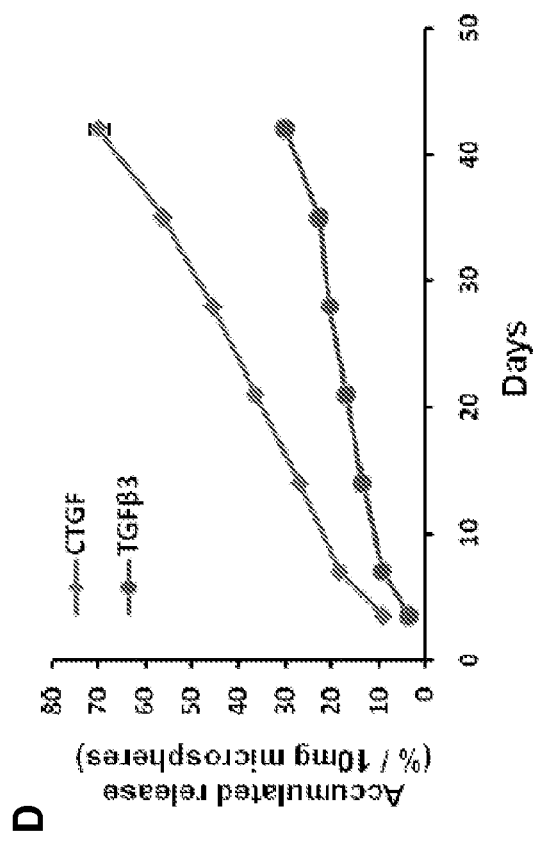

FIG. 14A-D
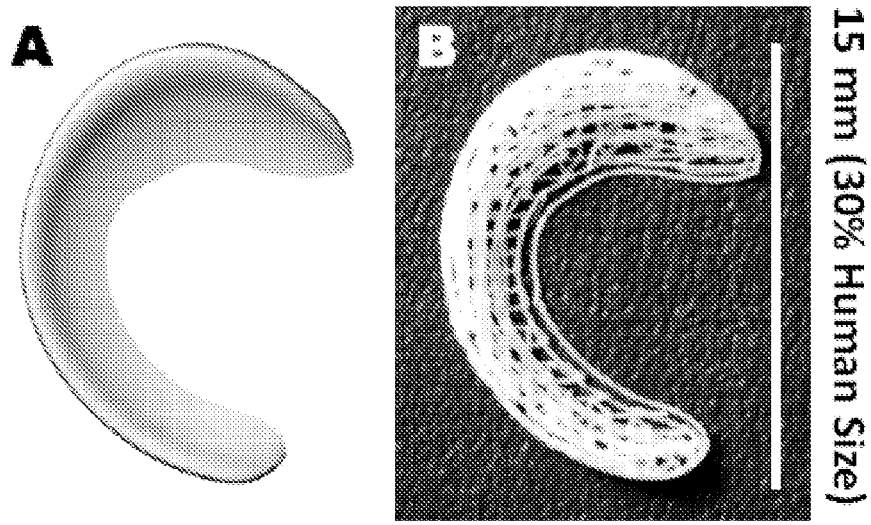
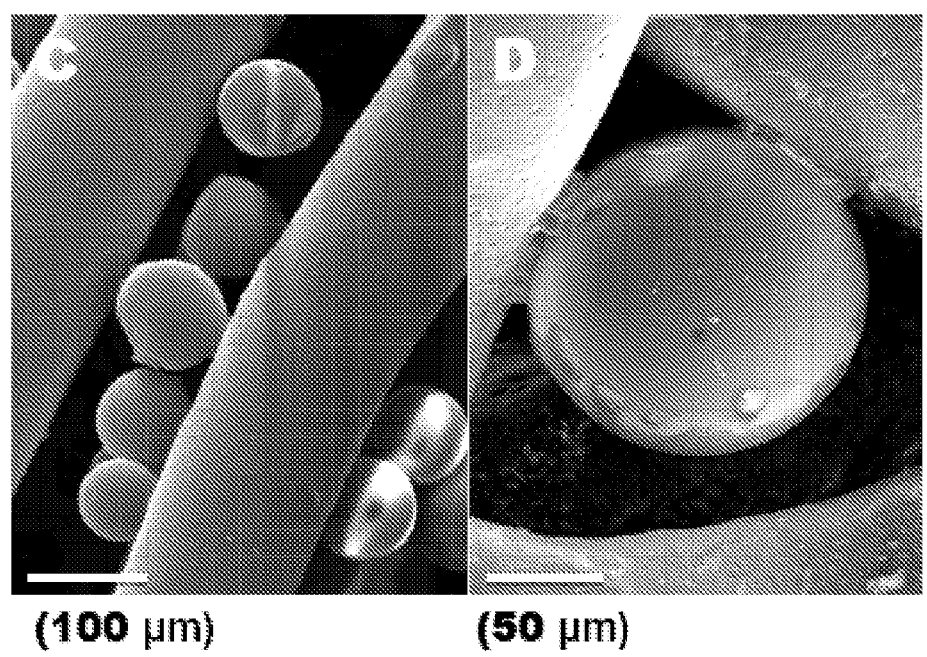

FIG. 14E-F
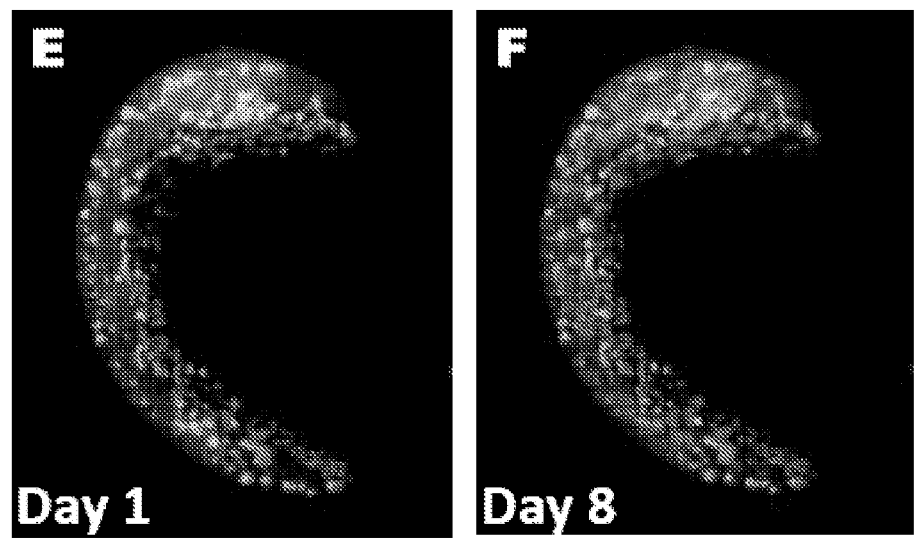
LEGEND
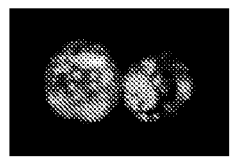 Dextran (40 kDa)-Fluorescein in 50:50 PLGA µS
 Dextran (10 kDa)-Alex Fluor® 546 in 75:25 PLGA µS

DERIVATION OF FIBROCHONDROCYTES FROM PROGENITOR CELLS

CROSS-REFERENCE TO RELATED APPLICATIONS

The present application claims the benefit of priority to PCT International Application No. PCT/US11/54660 filed Oct. 3, 2011, which claims the benefit U.S. Provisional Application Ser. No. 61/388,791 filed Oct. 1, 2010, each of which is incorporated herein by reference in their entireties.

MATERIAL INCORPORATED-BY-REFERENCE

Not Applicable.

STATEMENT REGARDING FEDERALLY SPONSORED RESEARCH OR DEVELOPMENT

This invention was made with government support under R01DE018248 awarded by the National Institutes of Health. The government has certain rights in the invention.

FIELD OF THE INVENTION

The present invention generally relates to fibrochondrocytes.

BACKGROUND OF THE INVENTION

Fibrocartilage is a specialized tissue sharing characteristics of fibrous tissue and, to various degrees, cartilage. Fibrocartilage consists of a mixture of white fibrous tissue and cartilaginous tissue in various proportions. It owes its flexibility and toughness to fibrous tissue, and its elasticity to cartilaginous tissue. Fibrocartilage is the only type of cartilage that contains type I collagen in addition to the normal type II.

In humans, fibrocartilage is found in knee meniscus, ligament/tendon insertion to bone, the intervertebra disc (IVD), and the temporomandibular joint (TMJ). All fibrocartilage tissues are intrinsically recalcitrant to regeneration. Few therapies exist to regenerate fibrocartilage tissues.

Cells of fibrocartilage are not well understood but are frequently referred to as fibrochondrocytes. Although mesenchymal stem cells (MSCs) are the presumably source of fibrochondrocytes in development, there is little evidence that postnatal fibrochondrocytes derive from postnatal MSCs. In comparison with known and recently demonstrated pathways of osteogenic, chondrogenic, and adipogenic differentiation, little is known about the induction cues and signaling pathways for fibrochondrogenic differentiation. It has been reported that connective tissue growth factor (CTGF) alone induces fibroblastic differentiation of MSCs (Lee et al. 2010 J Clin Investig (in press). It has also been reported that CTGF-mediated fibrogenesis is regulated by a separate signaling pathway from transforming growth factor β3 (TGFβ3)-mediated chondrogenesis (Tuli et al. 2003 J Biol Cem 17(278), 41227-41236).

Prior to the present disclosure, there existed no reliable way to differentiate stem cells or progenitor cells into fibrochondrocytes. Conventional methods utilize cyclic mechanical stimulus to induce fibrochondrogenic differentiation but yields unreliable cells.

SUMMARY OF THE INVENTION

Disclosed herein is a new approach towards differentiation of progenitor cells into fibrochondrocytes or fibrochondrocyte-like cells using chemical factors.

One aspect provides a culture medium for generating fibrochondrocyte or fibrochondrocyte-like cells. Some embodiments of the culture medium include CTGF encapsulated in a first microsphere and TGFβ3 encapsulated in a second microsphere. In some configurations of the culture medium, the first microsphere and the second microsphere have different release profiles.

In some embodiments of the culture medium, the first microsphere is a 50:50 poly(lactic-co-glycolic acid) (PLGA) microsphere. In some embodiments of the culture medium, the second microsphere is a 75:25 PLGA microsphere.

In some embodiments of the culture medium, CTGF has a concentration of about 10 to about 1000 ng/mL. In some embodiments of the culture medium, TGFβ3 has a concentration of about 1 to about 1000 ng/mL. In some embodiments of the culture medium, CTGF has a concentration of about 100 ng/mL. In some embodiments of the culture medium, TGFβ3 has a concentration of about 10 ng/mL.

In some embodiments, the culture medium includes a fibroblastic induction supplement. In some embodiments, the culture medium includes a chondrogenic induction supplement. In some embodiments, the culture medium includes a fibroblastic induction supplement and a chondrogenic induction supplement.

Another aspect provides a method of forming fibrochondrocytes or fibrochondrocyte-like cells. In some embodiments, the method includes contacting a progenitor cell and a culture medium described herein. In some embodiments, the method includes contacting a progenitor cell with CTGF and TGFβ3 sequentially or concurrently. In some embodiments, the method includes culturing the progenitor cell so as to form a fibrochondrocyte or fibrochondrocyte-like cell.

In some embodiments of the method, the first microsphere releases CTGF earlier or faster than the second microsphere releases TGFβ3. In some embodiments of the method, the first microsphere releases CTGF later or slower than the second microsphere releases TGFβ3. In some embodiments of the method, the first microsphere releases CTGF about the same as the second microsphere releases TGFβ3. In some embodiments of the method, the progenitor cell is contacted with CTGF followed sequentially by contact with TGFβ3. In some embodiments of the method, the progenitor cell is contacted with TGFβ3 followed sequentially by contact with CTGF. In some embodiments of the method, the progenitor cell is contacted concurrently with TGFβ3 and CTGF.

In some embodiments of the method, culturing the progenitor cell occurs for about two days to about five days. In some embodiments of the method, culturing the progenitor cell occurs for at least about two days. In some embodiments of the method, culturing the progenitor cell occurs for at least about three days. In some embodiments of the method, culturing the progenitor cell occurs for at least about four days. In some embodiments of the method, culturing the progenitor cell occurs for at least about five days.

In some embodiments of the method, the number of formed fibrochondrocytes or fibrochondrocyte-like cells is at least about 100% greater than the number of fibrochondrocytes or fibrochondrocyte-like cells formed under culture conditions not comprising CTGF and TGFβ3.

In some embodiments of the method, fibrochondrocytes or fibrochondrocyte-like cells display one or more of: increased collagen (COL) deposition; increased proteoglycan (PG) deposition; increased glycosaminoglycan (GAG) deposition; increased proCOL-I+; or increased proCOL-IIα+, as compared to the progenitor cell.

In some embodiments of the method, the progenitor cell is a mesenchymal stem cell. In some configurations of the method, the progenitor cell is a human mesenchymal stem cell.

Another aspect provides a method of forming a fibrocartilage tissue. In some embodiments, the method of forming a fibrocartilage tissue includes providing a scaffold comprising an effective amount of the culture medium described above; placing the scaffold in fluid communication with a progenitor cell; inducing migration of the progenitor cell into or onto the scaffold; and inducing formation of a fibrochondrocyte or fibrochondrocyte-like cell from the progenitor cell; wherein, the scaffold does not comprise a transplanted cell.

Another aspect provides a method of treating a subject having a fibrocartilage tissue defect. In some embodiments, the method of treating includes implanting into a subject in need thereof a scaffold comprising an effective amount of the culture medium described above; wherein the scaffold does not comprise a transplanted cell prior to implant; the effective amount of the culture medium induces migration of a progenitor cell into or onto the scaffold; and the effective amount of the culture medium induces formation of a fibrochondrocyte or fibrochondrocyte-like cell from the progenitor cell.

Another aspect provides a fibrocartilage tissue construct. In some embodiments, the fibrocartilage tissue construct includes a scaffold comprising an effective amount of the culture medium described above; wherein the scaffold does not comprise a transplanted cell; the effective amount of the culture medium can induce migration of a progenitor cell into or onto the scaffold when the scaffold is in fluid communication with the progenitor cell; and the effective amount of the culture medium can induce formation of an fibrochondrocyte or fibrochondrocyte-like cell from the progenitor cell.

In some embodiments of methods or construct, the scaffold includes a biocompatible matrix material. In some embodiments of methods or construct, the scaffold comprises poly(lactic-co-glycolic acid) (PLGA). In some embodiments of methods or construct, the scaffold comprises at least one physical channel. In some embodiments of methods or construct, the scaffold comprises at least two layers. In some embodiments of methods or construct, the scaffold comprises a first layer and a second layer, the first layer comprises CTGF and the second layer comprises TGF-β3.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 8 is a series of images and a pair of line and scatter plots showing in-cell Western (Odyssey) +100 ng/ml CTGF. FIG. 8B is a line and scatter plot of p-FAK/DRAQ5™ upon CTGF as a function of time from 0 minutes to 4 hours for control FAK inh and 38 inh. FIG. 8C is a line and scatter plot of p-38/DRAQ5 upon CTGF as a function of time from 0 minutes to 4 hours for control FAK inh, and p38 inh.

FIG. 9 is a series of images and a pair of line and scatter plots showing in-cell Western (Odyssey) +10 ng/ml TGFβ3. FIG. 9B is a line and scatter plot of p-FAK/DRAQ5 upon TGFβ3 as a function of time from 0 minutes to 4 hours for control, FAK inh, and p38 inh. FIG. 9C is a line and scatter plot of p-38/DRAQ5 upon TGFβ3 as a function of time from 0 minutes to 4 hours for control, FAK inh, and p38 inh.

FIG. 12 is a series of bar graphs showing mRNA expression with inhibitors at 4 weeks.

FIG. 13 is a series of images and a line and scatter plot showing fibrocartilaginous differentiation of hMSCs by control-release of two growth factors from PLGA µS in 3D fibrin gel. In vitro release profile shows sustained and sequential release of CTGF and TGFβ3 up to 42 days (FIG. 13A). H&E (FIG. 13B), AB (FIG. 13C) and PR (FIG. 13D) staining revealed fibrocartilaginous differentiation by 4 wks (scale: 100 µm). Additional information regarding methodology is provided in Example 1.

FIG. 14 is a series of images showing engineered fibrocartilage tissue. FIG. 14A is a 3D rendering of a knee meniscus. FIG. 14B is an image of a scaffold having the correct anatomical shape of a knee meniscus. FIG. 14C is an image of microsphere adhesion to matrix strands of the scaffold at a scale of 100 μm. FIG. 14D is an image of microsphere adhesion to matrix strands of the scaffold at a scale of 50 μm. FIG. 14E is an immunofluorescence image of the scaffold at day 1 with Dextran (40 kDa)-Fluorescein in 50:50 PLGA microspheres and Dextran (10 kDa)-Alex Fluor® 546 in 75:25 PLGA microspheres. FIG. 14F is an immunofluorescence image of the scaffold at day 8 with Dextran (40 kDa)-Fluorescein in 50:50 PLGA microspheres and Dextran (10 kDa)-Alex Fluor® 546 in 75:25 PLGA microspheres.

FIG. 16A-C are H&E stained sections of outer, middle, and inner sections of the harvested scaffold. FIG. 16D-F are Picrosiriuos Red (PR) stained sections of outer, middle, and inner sections of the harvested scaffold. FIG. 16H-J are Alcian Blue (AB) stained sections of outer, middle, and inner sections of the harvested scaffold.

FIG. 17A-C are H&E-stained sections of outer, middle, and inner sections of a harvested native meniscus. FIG. 17D-F are H&E-stained sections of outer, middle, and inner sections of the harvested scaffold.

DETAILED DESCRIPTION OF THE INVENTION

Figure 1:
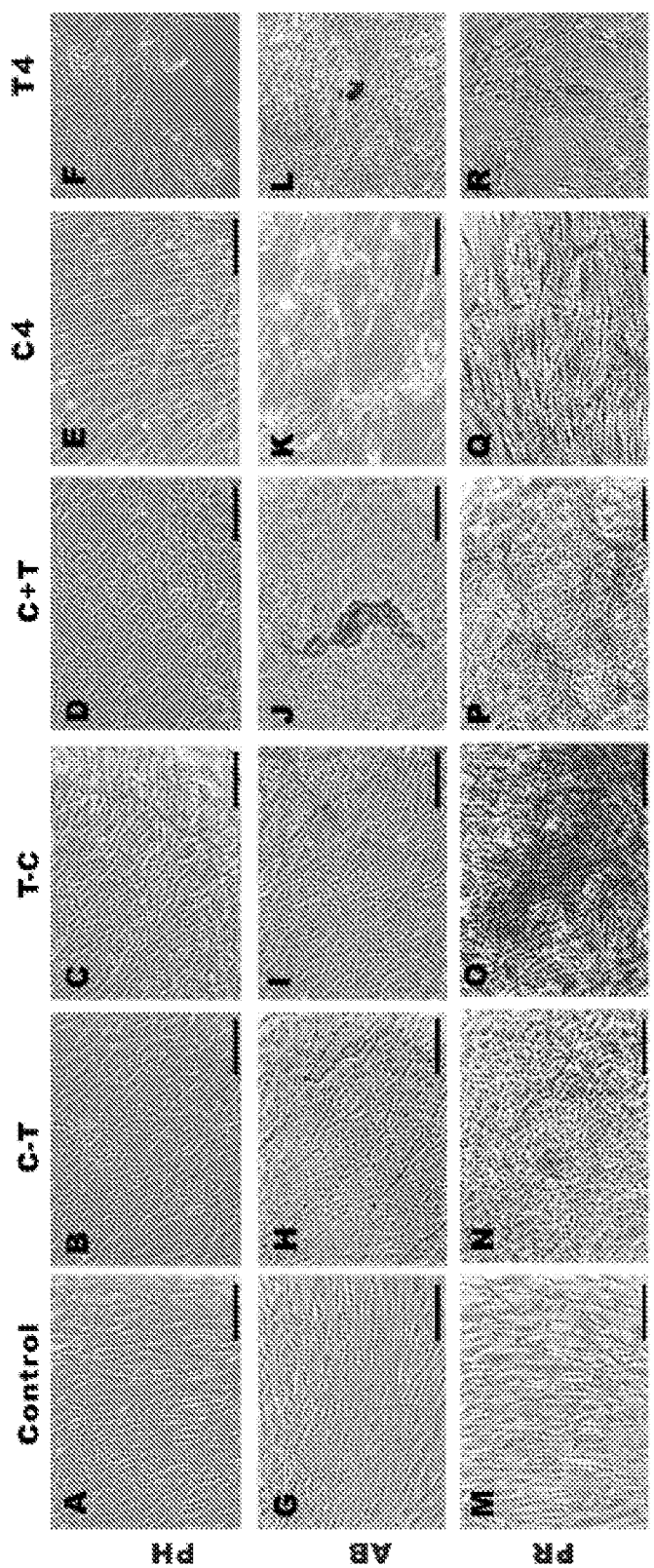
FIG. 1 is a series of images showing fibrochondrogenic differentiation of human mesenchymal stem cells (hMSCs) in 2D by 4 wks. Sections were stained with hematoxylin and eosin (H&E) (FIG. 1A-F), AB (FIG. 1G-L) and PR (FIG. 1M-R). (scales: 200 µm).

The present disclosure is based at least in part on the discovery that CTGF-mediated fibrogenesis is regulated by a separate pathway from CTGF and TGFβ3-mediated chondrogenesis.

Disclosed herein is a new approach towards differentiation of progenitor cells, for example human mesenchymal cells (hMSCs), into fibrochondrocytes, or fibrochondrocyte-like cells, using chemical factors, such as by the treatment of CTGF and TGFβ3. Such fibrochondrocytes or fibrochondrocyte-like cells can serve as a source of therapeutic cells for the regeneration of fibrocartilage tissues. Also disclosed herein is the generation and regeneration of fibrocartilage tissues.

As demonstrated herein, hMSCs treated with CTGF and TGFβ3 showed significant increases in markers for fibrochondrocyte differentiation (see Example 1). The inducement of in vivo or ex vivo differentiation of hMSCs into fibrochondrocytes, or fibrochondrocyte-like cells, as described herein, can be applied to fibrocartilage tissue engineering and fibrocartilage tissue regeneration (see Example 2).

In contrast to conventional methods, the present disclosure provides, in some embodiments, methods of differentiation based at least in part, or substantially, on chemical factors. Such approaches provide for larger scale differentiation and expansion, useful for tissue engineering or tissue regeneration.

Progenitor Cells

A progenitor cell, as that term is used herein, is a precursor to a fibrochondrocyte or fibrochondrocyte-like cell and can differentiate in the presence of CTGF and TGFβ3. A progenitor cell can be a multipotent cell. A progenitor cell can be self-renewing. For example, a progenitor cell can be a mesenchymal stem cell (e.g., a human mesenchymal stem cell). The progenitor cell can be substantially less differentiated than a fibrochondrocyte or fibrochondrocyte-like cell. For example, a progenitor cell can be freshly isolated or not pre-treated with growth factors before being further cultured with compositions including CTGF or TGFβ3 described herein. Progenitor cells can be isolated, purified, and/or cultured by a variety of means known to the art Methods for the isolation and culture of tissue progenitor cells are discussed in, for example, Vunjak-Novakovic and Freshney (2006) Culture of Cells for Tissue Engineering, Wiley-Liss, ISBN 0471629359. For example, mesenchymal stem cells can be isolated from bone marrow and culture-expanded (see e.g., Example 1).

In various embodiments, a progenitor cell is a precursor to a fibrochondrocyte or fibrochondrocyte-like cell and differentiates under culture conditions including sequential or concurrent provision of CTGF and TGFβ3 described herein. In some embodiments, a progenitor cell does not display a fibrocartilaginous matrix. For example, a progenitor cell may not display COL deposition. As another example, a progenitor cell may not display PG deposition. As another example, a progenitor cell may not display GAG deposition. In some embodiments, a progenitor cell does not display a fibrochondrocyte-specific marker, such as proCOL-I+ or proCOL-IIα+.

The tissue progenitor cells can be derived from the same or different species as the transplant recipient. For example, the progenitor cells can be derived from an animal, including, but not limited to, mammals, reptiles, and avians, more preferably horses, cows, dogs, cats, sheep, pigs, and chickens, and most preferably human.

Fibrochondrocyte or Fibrochondrocyte-Like Cells

In various embodiments, a fibrochondrocyte or fibrochondrocyte-like cell differentiates from a progenitor cell under culture conditions including sequential or concurrent provision of CTGF and TGFβ3 described herein. In some embodiments, a fibrochondrocyte or fibrochondrocyte-like cell displays a fibrocartilaginous matrix. For example, a fibrochondrocyte or fibrochondrocyte-like cell can display COL deposition. As another example, a fibrochondrocyte or fibrochondrocyte-like cell can display PG deposition. As another example, a fibrochondrocyte or fibrochondrocyte-like cell can display GAG deposition. In some embodiments, a fibrochondrocyte or fibrochondrocyte-like cell can display a fibrochondrocyte-specific marker, such as proCOL-I+ or proCOL-IIα+.

In some embodiments, a progenitor cell or a fibrochondrocyte or fibrochondrocyte-like cell can be transformed with a heterologous nucleic acid so as to express a bioactive molecule, or heterologous protein or to overexpress an endogenous protein. As an example, a progenitor cell or a fibrochondrocyte or fibrochondrocyte-like cell can be genetically modified to expresses a fluorescent protein marker. Exemplary markers include green fluorescent protein (GFP), enhanced green fluorescent protein (EGFP), blue fluorescent protein (BFP), cyan fluorescent protein (CFP), yellow fluorescent protein (YFP), and red fluorescent protein (RFP). As another example, a progenitor cell or a fibrochondrocyte or fibrochondrocyte-like cell can be genetically modified to express an angiogenesis-related factor, such as activin A, adrenomedullin, acidic fibroblast growth factor (aFGF), activin receptor-like kinase 1 (ALK1), activin receptor-like kinase 5 (ALK5), atrial natriuretic factor (ANF), angiogenin, angiopoietin-1, angiopoietin-2, angiopoietin-3, angiopoietin-4, angiostatin, angiotropin, angiotensin-2, AtT20-endothelial cell growth factor (AtT20-ECGF), betacellulin, basic fibroblast growth factor (bFGF), B61, basic fibroblast growth factor (bFGF) inducing activity, cadherins, cellular adhesion molecule regulatory factor (CAM-RF), cyclic guanosine 3',5'-monophosphate (cGMP) analogs, chondrocyte-derived inhibitor (ChDI), Corpus luteum angiogenic factor (CLAF), claudins, collagen, collagen receptors $\alpha_1\beta_1$ and $\alpha_2\beta_1$, connexins, cyclo-oxygenase-2 (Cox-2), endothelial cell-derived growth factor (ECDGF), endothelial cell growth (ECG), endothelial cell inhibitor (ECI), Alpha(v)-beta 3/alpha(v)-beta 5 integrin antagonist (EDM), epidermal growth factor (EGF), endothelial monocyte-activating polypeptide (EMAP), endoglin, endothelins, endostatin, endothelial cell growth inhibitor, endothelial cell-viability maintaining factor, endothelial differentiation shpingolipid G-protein coupled receptor-1 (EDG1), ephrins, erythropoietin (Epo), hepatocyte growth factor (HGF), tumor necrosis factor alpha (TNF-alpha), transforming growth factor beta (TGF-beta), phosphorylase/platelet-derived endothelial cell growth factor (PD-ECGF), platelet-derived growth factor (PDGF), insulin-like growth factor (IGF), interleukin 8 (IL8), growth hormone, fibrin fragment E, fibroblast growth factor 5 (FGF-5), fibronectin and fibronectin receptor $\alpha5\beta1$, Factor X, heparin-binding EGF-like growth factor (HB-EGF), heparin-binding neurotrophic factor (HBNF), hepatocyte growth factor (HGF), human uterine angiogenesis factor (HUAF), heart derived inhibitor of vascular cell proliferation, interferon gamma (IFN-gamma), interleukin 1 (IL1), Insulin-like growth factor-2 (IGF-2), integrin receptors, Kaposi fibroblast growth factor (K-FGF), Leukemia inhibitory factor (LIF), leiomyoma-derived growth factor, Monocyte chemotactic protein (MCP-1), macrophage-derived growth factor, monocyte-derived growth factor, macrophage-derived endothelial cell inhibitor (MD-ECI), Monocyte-Derived Endothelial Cell Inhibitory Factor (MECIF), matrix metalloproteinase-2 (MMP 2), matrix metalloproteinase 3 (MMP3), matrix metalloproteinase 9 (MMP9), urokiase plasminogen activator, neuropilin (NRP1, NRP2), neurothelin, nitric oxide donors, nitric oxide synthases (NOSs), notch, occludins, zona occludins, oncostatin M, platelet-derived growth factor beta polypeptide (PDGF-B), Platelet-derived growth factor (PDGF) receptors, Platelet derived growth factor receptor-beta (PDGFR-$\beta$), Plasminogen activator inhibitor-2 (PAI-2), Platelet factor 4 (PF4), Placental growth factor (P1GF), Prokineticin receptor 1 (PKR1), Prokineticin receptor 2 (PKR2), Peroxisome proliferator-activated receptor gamma (PPAR-gamma), PPAR-gamma ligands, phosphodiesterase, prolactin, prostacyclin, protein S, smooth muscle cell-derived growth factor, smooth muscle cell-derived migration factor, sphingosine-1-phosphate-1 (S1P1), spleen tyrosine kinase (Syk), SH2 domain-containing protein 76 (SLP76), tachykinins, TGF-beta, tyrosine kinase with immunoglobulin-like and EGF-like domains 1 (Tie 1), tyrosine kinase with immunoglobulin-like and EGF-like domains 1 (Tie2), TGF-$\beta$, and TGF-$\beta$ receptors, tissue inhibitors of metalloproteinases (TIMPs), tumor necrosis factor beta (TNF-beta), transferrin, thrombospondin, urokinase, Vascular endothelial growth factor A (VEGF-A), Vascular endothelial growth factor B (VEGF-B), Vascular endothelial growth factor C (VEGF-C), Vascular endothelial growth factor D (VEGF-D), Vascular endothelial growth factor E (VEGF-E), Vascular endothelial growth factor (VEGF), Vascular endothelial growth factor isoform 164 (VEGF-164), Vascular endothelial growth factor inhibitor (VEGI), Endocrine gland-derived endothelial growth factor (EG-VEGF), Vascular endothelial growth factor receptors (VEGF receptors), Platelet factor 4 (PF4), 16 kDa fragment of prolactin, prostaglandins E1 and E2, steroids, heparin, 1-butyryl glycerol (monobutyrin), and/or nicotinic amide. As another example, a progenitor cell or a fibrochondrocyte or fibrochondrocyte-like cell can be transfected with genetic sequences that are capable of reducing or eliminating an immune response in a host (e.g., expression of cell surface antigens such as class I and class II histocompatibility antigens can be suppressed). This can allow the transplanted cells to have reduced chance of rejection by the host.

Culturing and Differentiation Methods

Described herein are exemplary methods to induce fibrochondrogenic differentiation of progenitor cells by sequential or concurrent treatment of growth factors, such as connective tissue growth factor (CTGF) and transforming growth factor $\beta3$ (TGF$\beta3$) on substrates, such as monolayer or 3D pellet culture of hMSCs (see Example 1). As shown herein, sequential treatment of hMSCs with CTFG and TGF$\beta3$ more readily induced fibrocartilaginous differentiation than concurrent application, although both methods can result in induction of fibrochondrocytes (see Example 1).

A progenitor cell can be contacted with CTGF and TGF$\beta3$ sequentially or simultaneously so as to stimulate differentiation of fibrochondrocyte or fibrochondrocyte-like cells. For example, progenitor cells can be contacted with CTGF followed by TGF$\beta3$. As another example, progenitor cells can be contacted with TGF$\beta3$ followed by CTGF. As another example, progenitor cells can be contacted concurrently with CTGF and TGF$\beta3$.

Progenitor cells can be cultured by a variety of means known to the art. Progenitor cells can be incubated with CTGF or TGF$\beta3$ under conditions allowing differentiation to fibrochondrocyte or fibrochondrocyte-like cells. Methods of culturing progenitor cells are generally known in the art and such methods can be adapted so as to provide optimal conditions for differentiation of progenitor cells contacted with CTGF or TGF$\beta3$ (see e.g., Vunjak-Novakovic and Freshney (2006) Culture of Cells for Tissue Engineering, Wiley-Liss, ISBN 0471629359).

CTGF is available from a variety of commercial sources (e.g., Santa Cruz Biotechnology, Inc., Santa Cruz, Calif.). Preferably, the connective tissue growth factor is preferably human connective tissue growth factor (e.g., Accession No. NP_001892).

CTGF can be supplied at, for example, a concentration of about 0 to about 1000 ng/mL. For example, CTGF can be present at a concentration of about 10, about 20, about 30, about 40, about 50, about 60, about 70, about 80, about 90, about 100, about 110, about 120, about 130, about 140, about 150, about 160, about 170, about 180, about 190, about 200, about 250, about 300, about 350, about 400, about 450, about 500, about 550, about 600, about 700, about 750, about 800, about 850, about 900, about 950, or about 1000 ng/mL. For example, CTGF can be present at a concentration of about 100 ng/mL (see e.g., Example 1).

TGF$\beta3$ is available from a variety of commercial sources (e.g., Santa Cruz Biotechnology, Inc., Santa Cruz, Calif.). The connective tissue growth factor can be human TGF$\beta3$ (e.g., Accession No. NM_003239) (e.g., Avotermin). TGF$\beta3$ can be supplied at, for example, a concentration of about 0 to about 1000 ng/mL. For example, TGF$\beta3$ can be present at a concentration of about 1, about 2, about 3, about 4, about 5, about 6, about 7, about 8, about 9, about 10, about 20, about 30, about 40, about 50, about 60, about 70, about 80, about 90, about 100, about 110, about 120, about 130, about 140, about 150, about 160, about 170, about 180, about 190, about 200, about 250, about 300, about 350, about 400, about 450, about 500, about 550, about 600, about 700, about 750, about 800, about 850, about 900, about 950, or about 1000 ng/mL. For example, TGFβ3 can be present at a concentration of about 10 ng/mL (see e.g., Example 1).

Compositions including CTGF or TGFβ3 can be formulated or encapsulated for controlled release, as described further below. For example, compositions including CTGF or TGFβ3 can be encapsulated in microspheres, such as PLGA microspheres (see e.g., Example 1). Differing PLGA ratios can be used to provide sequential release of CTGF and TGFβ3. For example, a composition including CTGF can be encapsulated in 50:50 PLGA microspheres. As another example, a composition including TGFβ3 can be encapsulated in 75:25 PLGA microspheres. Encapsulated compositions including CTGF or TGFβ3 can be embedded in a biocompatible matrix A (e.g., a 3D fibrin gel) loaded with progenitor cells (e.g., mesenchymal stem cells) and cultured in vitro.

Progenitor cells can be cultured by a variety of means known to the art. For example, progenitor cells can be plated (e.g., about 100,000 cells per well) for 2D culture. As another example, progenitor cells can be centrifuged (e.g., about 2 million cells) to form a 3D pellet. Monolayer (2D) or 3D cell pellets can be cultured in a growth medium. Monolayer (2D) or 3D cell pellets can be treated with CTGF and TGFβ3 sequentially or concurrently. Administration of CTGF or TGFβ3 can occur over about one week to about five weeks. For example, administration of CTGF or TGFβ3 can occur over about two weeks, about three weeks, or about four weeks.

An induction medium can be provided in conjunction with CTGF or TGFβ3 (e.g., as a component of encapsulated composition or provided separately. For example, a fibroblastic induction supplement can be included in or with the CTGF treatment. An exemplary fibroblastic induction supplement can include ascorbic acid (see e.g., Example 1). As another example, a chondrogenic induction supplement can be included in or with the TGFβ3 treatment. An exemplary chondrogenic induction supplement can include one or more of ITS+1 solution, sodium pyruvate, ascorbic acid 2-phosphate, proline, or dexamethasone (see e.g., Example 1).

Methods described herein can increase the number of formed fibrochondrocyte or fibrochondrocyte-like cells as compared to conventional methods. For example, culture methods described herein can increase differentiation of fibrochondrocyte or fibrochondrocyte-like cells from progenitor cells by at least about 10%. For example, culture methods described herein can increase differentiation of fibrochondrocyte or fibrochondrocyte-like cells from progenitor cells by at least about 50%. For example, culture methods described herein can increase differentiation of fibrochondrocyte or fibrochondrocyte-like cells from progenitor cells by at least about 100%. As another example, culture methods described herein can increase differentiation of fibrochondrocyte or fibrochondrocyte-like cells from progenitor cells by at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, or at least about 1,000%.

In some embodiments, a progenitor cell or a fibrochondrocyte or fibrochondrocyte-like cell can be co-cultured with one or more additional cell types. Such additional cell types can include (but are not limited to) cardiac cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, or chondrocytes.

Scaffold

Various embodiments described herein employ a scaffold or matrix material. For example, a composition including CTGF or TGFβ3 can be included in or on a scaffold.

The scaffold optionally does not comprise a transplanted mammalian cell, i.e., no cell is applied to the scaffold; any cell present in the scaffold migrated into the scaffold.

A scaffold can be fabricated with any matrix material recognized as useful by the skilled artisan. A matrix material can be a biocompatible material that generally forms a porous, microcellular scaffold, which provides a physical support for cells migrating thereto. Such matrix materials can: allow cell attachment and migration; deliver and retain cells and biochemical factors; enable diffusion of cell nutrients and expressed products; or exert certain mechanical and biological influences to modify the behavior of the cell phase. The matrix material generally forms a porous, microcellular scaffold of a biocompatible material that provides a physical support and an adhesive substrate for recruitment and growth of cells during in vitro or in vivo culturing.

Suitable scaffold and matrix materials are discussed in, for example, Ma and Elisseeff, ed. (2005) Scaffolding In Tissue Engineering, CRC, ISBN 1574445219; Saltzman (2004) Tissue Engineering: Engineering Principles for the Design of Replacement Organs and Tissues, Oxford ISBN 019514130X. For example, matrix materials can be, at least in part, solid xenogenic (e.g., hydroxyapatite) (Kuboki et al. 1995 Connect Tissue Res 32, 219-226; Murata et al. 1998 Int J Oral Maxillofac Surg 27, 391-396), solid alloplastic (polyethylene polymers) materials (Saito and Takaoka 2003 Biomaterials 24 2287-93; Isobe et al. 1999 J Oral Maxillofac Surg 57, 695-8), or gels of autogenous (Sweeney et al. 1995. J Neurosurg 83, 710-715), allogenic (Bax et al. 1999 Calcif Tissue Int 65, 83-89; Viljanen et al. 1997 Int J Oral Maxillofac Surg 26, 389-393), or alloplastic origin (Santos et al. 1998. J Biomed Mater Res 41, 87-94), and combinations of the above (Alpaslan et al. 1996 Br J of Oral Maxillofac Surg 34, 414-418).

The matrix comprising the scaffold can have an adequate porosity and an adequate pore size so as to facilitate cell recruitment and diffusion throughout the whole structure of both cells and nutrients. The matrix can be biodegradable providing for absorption of the matrix by the surrounding tissues, which can eliminate the necessity of a surgical removal. The rate at which degradation occurs can coincide as much as possible with the rate of tissue or organ formation. Thus, while cells are fabricating their own natural structure around themselves, the matrix is able to provide structural integrity and eventually break down, leaving the neotissue, newly formed tissue or organ which can assume the mechanical load. The matrix can be an injectable matrix in some configurations. The matrix can be delivered to a tissue using minimally invasive endoscopic procedures.

The scaffold can comprise a matrix material having different phases of viscosity. For example, a matrix can have a substantially liquid phase or a substantially gelled phase. The transition between phases can be stimulated by a variety of factors including, but limited to, light, chemical, magnetic, electrical, and mechanical stimulus. For example, the matrix can be a thermosensitive matrix with a substantially liquid phase at about room temperature and a substantially gelled phase at about body temperature. The liquid phase of the matrix can have a lower viscosity that provides for optimal distribution of growth factors or other additives and injectability, while the solid phase of the matrix can have an elevated viscosity that provides for matrix retention at or within the target tissue.

The scaffold can comprise one or more layers, each with the same or different matrix materials. For example, a scaffold can comprises at least two layers, at least three layers, at least four layers, or more. As another example, a scaffold can comprise a first layer comprising a first matrix material and a second layer comprising a second matrix material. As another example, a scaffold can comprise a first layer comprising CTGF and a second layer comprising TGFβ3. As another example, a scaffold can comprise a first layer comprising CTGF and TGFβ3 and a second layer comprising TGFβ3. As another example, a scaffold can comprise a first layer comprising CTGF and a second layer comprising TGFβ3 and CTGF.

Figure 16:
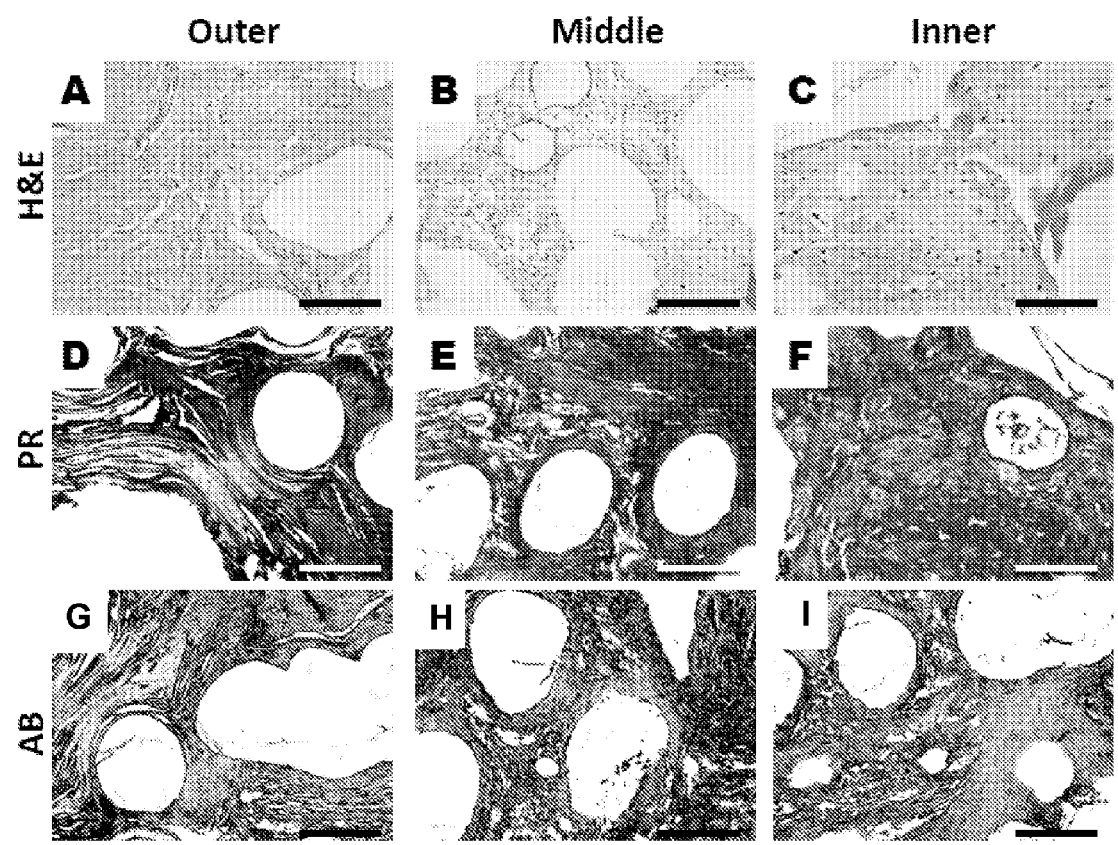
FIG. 16 shows a series of light microscopy images of sections of a partial meniscus replacement scaffold harvested at 2 months post-implantation.

As shown herein, discrete spatialization of TGFβ3 and CTGF can provide a collagen-rich matrix in the de novo tissues with more organized collagen structure in outer region (see e.g., Example 2; FIG. 16D) and proteoglycan-rich cartilaginous matrix more dominant toward inner region (see e.g., FIG. 16J), which is reminiscent of native meniscus. Thus, spatiotemporal delivery of CTGF and TGFβ3 can provide native-like multiphase fibrocartilage formation.

Figure 17:
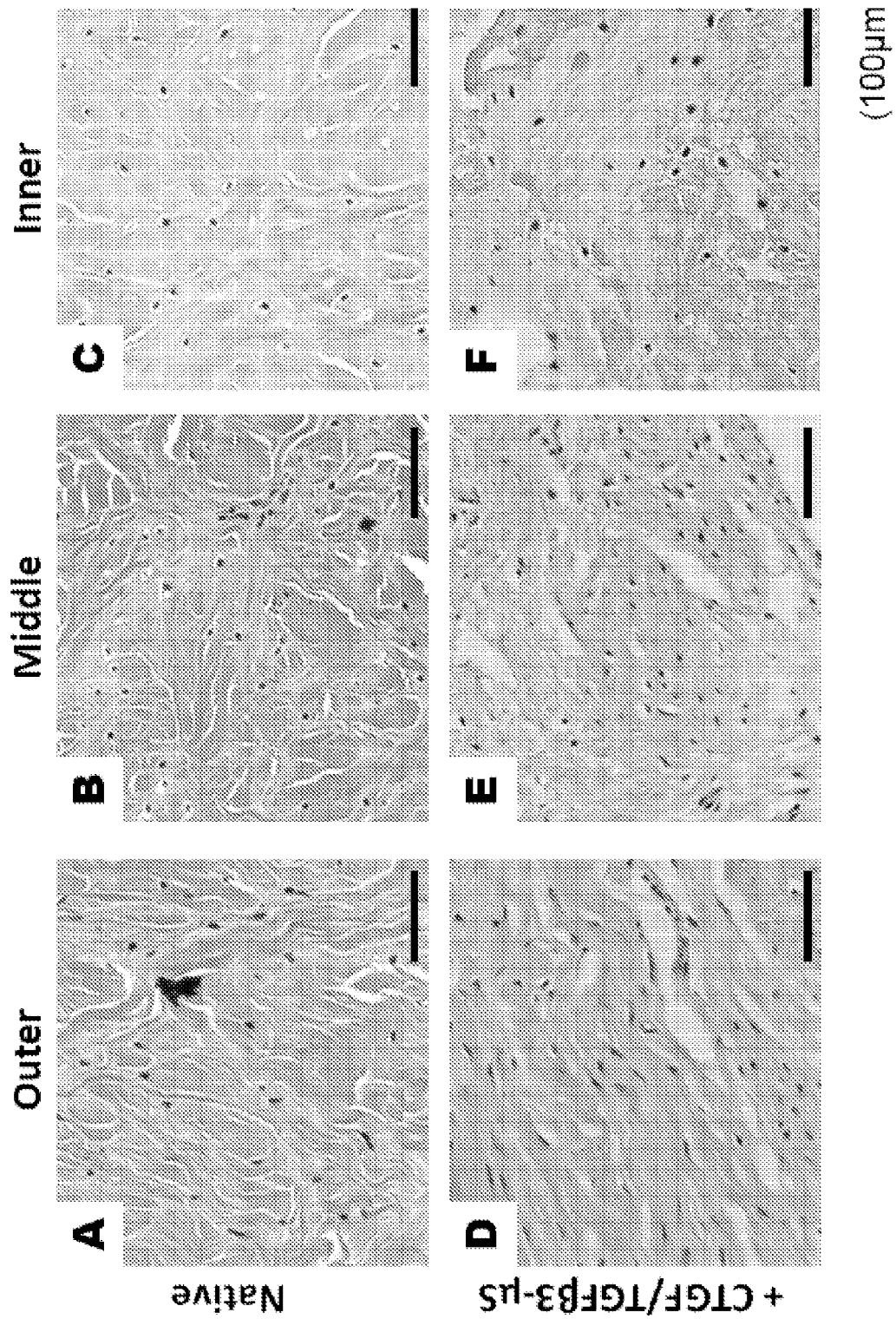
FIG. 17 shows a series of light microscopy images of sections of a partial meniscus replacement scaffold harvested at 2 months post-implantation.

Results also showed a partial meniscus replacement at 2 months post-implantation (See e.g., FIG. 17). Multiphase cell phenotypes were found in the regenerated meniscus with spatiotemporal delivery of CTGF and TGFβ3 (see e.g., FIG. 17D-F), which is reminiscent of those of native meniscus (see e.g., FIG. 17A-C). Round chondrocyte-like cells were populated in inner region (see e.g., FIG. 17F), whereas spindle shaped fibroblast-like cells were dominant in outer region (see e.g., FIG. 17D), In middle region, mixed population of fibrochondrocytes were observed (see e.g., FIG. 17E).

The scaffold can comprise a matrix material formed of synthetic polymers. Such synthetic polymers include, but are not limited to, polyurethanes, polyorthoesters, polyvinyl alcohol, polyamides, polycarbonates, polyvinyl pyrrolidone, marine adhesive proteins, cyanoacrylates, analogs, mixtures, combinations and derivatives of the above. Alternatively, the matrix can be formed of naturally occurring biopolymers. Such naturally occurring biopolymers include, but are not limited to, fibrin, fibrinogen, fibronectin, collagen, and other suitable biopolymers. Also, the matrix can be formed from a mixture of naturally occurring biopolymers and synthetic polymers.

The scaffold can include one or more matrix materials including, but not limited to, a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g. alginate), polyphosphazene, polyacrylate, or a polyethylene oxide-polypropylene glycol block copolymer. Matrices can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolefins, polyethylene oxide, polyvinyl alcohol, polytetrafluoroethylene (Teflon®), or nylon.

The scaffold can further comprise any other bioactive molecule, for example an antibiotic or an additional chemotactic growth factor or another osteogenic, dentinogenic, amelogenic, or cementogenic growth factor. In some embodiments, the scaffold is strengthened, through the addition of, e.g., human serum albumin (HSA), hydroxyethyl starch, dextran, or combinations thereof. Suitable concentrations of these compounds for use in the compositions of the application are known to those of skill in the art, or can be readily ascertained without undue experimentation.

The concentration of a compound or a composition in the scaffold will vary with the nature of the compound or composition, its physiological role, and desired therapeutic or diagnostic effect. A therapeutically effective amount is generally a sufficient concentration of therapeutic agent to display the desired effect without undue toxicity. For example, the matrix can include a composition comprising CTGF or TGFβ3 at any of the above described concentrations. The compound can be incorporated into the scaffold or matrix material by any known method. In some embodiments, the compound is imbedded in a gel, e.g., a collagen gel incorporated into the pores of the scaffold or matrix material or applied as a coating over a portion, a substantial portion, substantially all of, or all of the scaffold or matrix material.

Alternatively, chemical modification methods can be used to covalently link a compound or a composition to a matrix material. The surface functional groups of the matrix can be coupled with reactive functional groups of a compound or a composition to form covalent bonds using coupling agents well known in the art such as aldehyde compounds, carbodiimides, and the like. Additionally, a spacer molecule can be used to gap the surface reactive groups and the reactive groups of the biomolecules to allow more flexibility of such molecules on the surface of the matrix. Other similar methods of attaching biomolecules to the interior or exterior of a matrix will be known to one of skill in the art.

Pores and channels of the scaffold can be engineered to be of various diameters. For example, the pores of the scaffold can have a diameter range from micrometers to millimeters. In some embodiments, the pores of the matrix material include microchannels. Microchannels generally have an average diameter of about 0.1 μm to about 1,000 μm, e.g., about 50 μm to about 500 μm (for example about 100 μm, 150 μm, about 200 μm, about 250 μm, about 300 μm, about 350 μm, about 400 μm, about 450 μm, about 500 μm, or about 550 μm). One skilled in the art will understand that the distribution of microchannel diameters can have any distribution including a normal distribution or a non-normal distribution. In some embodiments, microchannels are a naturally occurring feature of the matrix material(s). In other embodiments, microchannels are engineered to occur in the matrix materials.

Several methods can be used for fabrication of porous scaffolds, including particulate leaching, gas foaming, electrospinning, freeze drying, foaming of ceramic from slurry, and the formation of polymeric sponge. Other methods can be used for fabrication of porous scaffolds include computer aided design (CAD) and synthesizing the scaffold with a bioplotter (e.g., solid freeform fabrication) (e.g., Bioplotter™, EnvisionTec, Germany).

Biologic drugs that can be added to compositions of the invention include immunomodulators and other biological response modifiers. A biological response modifier generally encompasses a biomolecule (e.g., peptide, peptide fragment, polysaccharide, lipid, antibody) that is involved in modifying a biological response, such as the immune response or tissue or organ growth and repair, in a manner that enhances a particular desired therapeutic effect, for example, the cytolysis of bacterial cells or the growth of tissue- or organ-specific cells or vascularization. Biologic drugs can also be incorporated directly into the matrix component. Those of skill in the art will know, or can readily ascertain, other substances which can act as suitable non-biologic and biologic drugs.

Compositions described herein can also be modified to incorporate a diagnostic agent, such as a radiopaque agent. The presence of such agents can allow the physician to monitor the progression of wound healing occurring internally. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents that can be utilized in the compositions can be readily ascertained by those of skill in the art and can include, for example, the use of radiolabeled fatty acids or analogs thereof.

The concentration of an agent in the composition will vary with the nature of the compound, its physiological role, and desired therapeutic or diagnostic effect. A therapeutically effective amount is generally a sufficient concentration of therapeutic agent to display the desired effect without undue toxicity. A diagnostically effective amount is generally a concentration of diagnostic agent which is effective in allowing the monitoring of the integration of the tissue graft, while minimizing potential toxicity. In any event, the desired concentration in a particular instance for a particular compound is readily ascertainable by one of skill in the art.

Molecular Engineering

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art. Generally, conservative substitutions can be made at any position so long as the required activity is retained.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[$Na^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (sRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12):

807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several sRNA molecule design programs using a variety of algorithms are known to the art (see e.g., Cenix algorithm, Ambion; BLOCK-iT™ RNAi Designer, Invitrogen; sRNA Whitehead Institute Design Tools, Bioinofrmatics & Research Computing). Traits influential in defining optimal sRNA sequences include G/C content at the termini of the siRNAs, Tm of specific internal domains of the sRNA, sRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, preferably in purified form, together with a suitable amount of carrier so as to provide the form for proper administration to the subject.

The formulation should suit the mode of administration. The agents of use with the current invention can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Methods described herein can provide therapeutic cells for the treatment of damage to tissues comprised of fibrocartilage. Also provided is a process of treating fibrocartilage-related injuries in a subject in need administration of a therapeutically effective amount of a composition including fibrochondrocyte or fibrochondrocyte-like cells. Torn fibrocartilage can be repaired using therapeutic fibrochondrocyte cells or fibrochondrocyte-like cells. Torn fibrocartilage can be repaired using scaffolds comprising compositions promoting recruitment of progenitor cells and differentiation into fibrochondrocyte-like cells. Fibrochondrocytes or fibrochondrocyte-like cells, or scaffolds comprising compositions promoting recruitment of progenitor cells and differentiation into fibrochondrocyte-like cells, can be administered or implanted for treatment of fibrocartilage-related injuries, such as to the knee meniscus, intervetebral discs, TMJ ligaments or tendons.

Methods described herein can provide, in various embodiments, treatment for damaged avascular fibrocartilage tissues, which are resistant to regeneration in the human body. As described herein, tissue such as fibrocartilage can be derived from progenitor cells such as mesenchymal stem cells (e.g., hMSCs). Such derivation can occur in vitro or in vivo. The methods can use a mixture of growth factors to stimulate progenitor cells, such as MSCs, to differentiate into fibrochondrocytes or fibrochondrocyte-like cells, which can then be used as therapeutic cells to generate fibrocartilage. A fibrochondrocyte differentiation media can be used directly with progenitor cells in vitro or in vivo. A fibrochondrocyte differentiation media can be used in or on an acelullar scaffold or a scaffold seeded with progenitor cells. Successful derivation of fibrocartilage can provide an option or supplement for repair treatments to tissues comprised of fibrocartilage.

Exemplary tissue for repair with compositions or methods described herein include, but are not limited to, damaged menisci (e.g., knee menisci), ligaments, tendons, intervertebra discs, temporomandibular joints, or triangular fibrocartilage area.

As an example, compositions described herein can be administered (e.g., through injection) between intervertebral discs to prevent or treat disc degeneration. As another example, compositions described herein can be administered to prevent or treat arthritis.

Various embodiments provide compositions and methods to recruit, home, or induce differentiation of progenitor cells by using a cell homing composition and subsequently promote or induce differentiation of recruited progenitor cells to form fibrochondrocyte or fibrochondrocyte-like cells using composition comprising CTGF or TGFβ3. A cell homing composition, an fibrochondrogenic composition, or a scaffold or matrix can be implanted in a subject so as to recruit endogenous progenitor cells into the scaffold or matrix material and differentiate recruited progenitor cells to fibrochondrocyte or fibrochondrocyte-like cells.

In some embodiments, methods of causing progenitor cells to migrate to a scaffold and differentiate to form fibrochondrocyte or fibrochondrocyte-like cells in the scaffold are provided. The method can include placing a scaffold containing a cell homing composition and an fibrochondrogenic composition in fluid communication with cells. As used herein, a scaffold is in "fluid communication" with a cell if the cell has no physical barrier (e.g., a basement membrane, areolar connective tissue, adipose connective tissue, etc.) preventing the cell from migrating to the scaffold. Without being bound to any particular mechanism, it is believed that the cell migrates to the scaffold along a moist path from its source, in response to the presence of a cell homing composition forming a concentration gradient to the cell, and thereby influencing the cell to migrate toward the higher concentrations of the cell homing composition in the scaffold.

The scaffold optionally does not comprise a transplanted mammalian cell, i.e., no cell is applied to the scaffold; any cell present in the scaffold migrated into the scaffold. A scaffold is generally understood to be a three-dimensional structure into which cells, tissue, vessels, etc., can grow, colonize and populate when the scaffold is placed into a tissue site. A scaffold of the method can be as discussed herein.

The compositions and methods described herein hold significant clinical value because of their ability to be recruit endogenous progenitor cells, thereby optionally avoiding transplant of cells to a subject.

Methods described herein are generally performed on a subject in need thereof. A subject in need of the therapeutic methods described herein can be a subject having, diagnosed with, suspected of having, or at risk for developing fibrocartilage-related degeneration or injury. A determination of the need for treatment will typically be assessed by a history and physical exam consistent with the disease or condition at issue. Diagnosis of the various conditions treatable by the methods described herein is within the skill of the art. The subject can be an animal subject, preferably a mammal, more preferably horses, cows, dogs, cats, sheep, pigs, mice, rats, monkeys, guinea pigs, and chickens, and most preferably a human.

An effective amount of composition including one or more of progenitor cells, fibrochondrocytes, fibrochondrocyte-like cells, CTGF, TGFβ3, or fibrocartilage described herein is generally that which can restore, at least partially or fully, structure or function to the tissue of interest. An effective amount of a scaffold comprising a composition including one or more of progenitor cells, fibrochondrocytes, fibrochondrocyte-like cells, CTGF, TGFβ3, or fibrocartilage described herein is generally that which can restore, at least partially or fully, structure or function to the tissue of interest.

An effective amount of a cell homing composition comprising CTGF or TGFβ3 can be that which can induce recruitment of progenitor cells or migration of progenitor cells. An effective amount of a fibrochondrogenic composition can be that which can induce differentiation of progenitor cells to fibrochondrocytes or fibrochondrocyte-like cells. An effective amount of a scaffold or matrix material containing cell homing composition and a fibrochondrogenic composition can be that which can induce recruitment of progenitor cells or migration of progenitor cells and induce differentiation of recruited progenitor cells to fibrochondrocytes or fibrochondrocyte-like cells. An effective amount of a scaffold or matrix material containing a cell homing composition and a fibrochondrogenic composition can be that which can recruit and induce migration of a sufficient number of progenitor cells and induce at least a portion of recruited progenitor cells to form a fibrochondrocytes or fibrochondrocyte-like cells so as to increase biological function of a tissue or organ. An effective amount of a scaffold or matrix material containing cell homing composition and a fibrochondrogenic composition can be that which restores function or appearance to tissue comprising some combination of cartilage, tendon, ligament or bone.

As an example, a subject in need can have a fibrocartilage cell or tissue deficiency of at least about 5%, about 10%, about 25%, about 50%, about 75%, about 90% or more, and compositions and methods described herein can provide an increase in number or function of fibrochondrocytes cells or fibrocartilage tissues. As another example, a subject in need can have damage to a tissue or organ, and the method can provide an increase in biological function of the tissue or organ by at least about 5%, about 10%, about 25%, about 50%, about 75%, about 90%, about 100%, or about 200%, or even by as much as about 300%, about 400%, or about 500%. As yet another example, the subject in need can have an fibrocartilage-related disease, disorder, or condition, and the method provides an engineered scaffold sufficient that can recruit progenitor cells and form fibrocartilage cells or tissue sufficient to ameliorate or stabilize the disease, disorder, or condition. For example, the subject can have a disease, disorder, or condition that results in the loss, atrophy, dysfunction, and/or death of fibrocartilage cells. In a further example, the subject in need can have an increased risk of developing a disease, disorder, or condition that is delayed or prevented by the method. As yet another example, the subject in need can have experienced death or dysfunction of fibrocartilage cells as the result of a side effect of a medication used for the treatment of another disease or disorder.

Implantation of an engineered construct is within the skill of the art. The scaffold or matrix material can be either fully or partially implanted into a tissue or organ of the subject to become a functioning part thereof. Preferably, the implant initially attaches to and communicates with the host through a cellular monolayer. Over time, endogenous cells can migrate into the scaffold to form tissue. The cells surrounding the engineered tissue can be attracted by biologically active materials, including biological response modifiers, such as polysaccharides, proteins, peptides, genes, antigens, and antibodies, which can be selectively incorporated into the matrix to provide the needed selectivity, for example, to tether the cell receptors to the matrix, stimulate cell migration into the matrix, or both. The matrix can comprise a gelled phase and interconnecting channels that allow for cell migration, augmented by both biological and physical-chemical gradients. For example, cells surrounding the implanted matrix can be attracted by biologically active materials including CTGF or TGFβ3. One of skill in the art will recognize and know how to use other biologically active materials that are appropriate for attracting cells to the matrix.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of composition including one or more of progenitor cells, fibrochondrocytes, fibrochondrocyte-like cells, CTGF, TGFβ3, or fibrocartilage can be employed in pure form or, where such forms exist, in pharmaceutically acceptable salt form and with or without a pharmaceutically acceptable excipient. For example, the compounds of the invention can be administered, at a reasonable benefit/risk ratio applicable to any medical treatment, in a sufficient amount to restore, at least partially or fully, structure or function to the tissue of interest.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

The specific therapeutically effective dose level for any particular subject will depend upon a variety of factors including the injury or disorder being treated and the severity of the injury or disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shamel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present invention will be decided by an attending physician within the scope of sound medical judgment.

Administration of compositions or scaffold comprising compositions described herein can occur as a single event or over a time course of treatment. For example, a composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for fibrocartilage-related degeneration or injury.

Various compositions described herein can be administered simultaneously or sequentially with another agent, such as an antibiotic, an antiinflammatory, or another agent. For example, a composition including one or more of progenitor cells, fibrochondrocytes, fibrochondrocyte-like cells, CTGF, TGFβ3, or fibrocartilage can be administered simultaneously with another agent, such as an antibiotic or an antiinflammatory. Simultaneous administration can occur through administration of separate compositions, each containing one or more of a composition described herein, an antibiotic, an antiinflammatory, or another agent. Simultaneous administration can occur through administration of one composition containing two or more of progenitor cells, fibrochondrocytes, fibrochondrocyte-like cells, CTGF, TGFβ3, fibrocartilage, an antibiotic, an antiinflammatory, or another agent. Compositions described herein can be administered sequentially with an antibiotic, an antiinflammatory, or another agent. For example, a composition described herein can be administered before or after administration of an antibiotic, an antiinflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the invention.

Delivery systems may include, for example, an infusion pump which may be used to administer the agent or composition in a manner similar to that used for delivering insulin or chemotherapy to specific organs or tumors. Typically, using such a system, an agent or composition is administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to progenitor cells, fibrochondrocytes, fibrochondrocyte-like cells, CTGF, TGFβ3, culture medium, induction supplement, or fibrocartilage. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Cell isolation and differentiation: Human mesenchymal stem cells (hMSCs) were isolated from fresh whole bone marrow samples of two anonymous adult donors (age range: 20-25 yrs old) (AllCells, Berkeley, Calif.). Mononucleated and adherent cells were purified by centrifugation through a density gradient (Ficoll-Paque) per our prior methods (Marion and Mao 2006 Methods Enzymol 420, 339-361) and using negative selection following manufacturer's protocols (RosetteSep, StemCell Technologies, Vancouver, Canada) to remove hematopoietic cells and other differentiated cells. P2 or 3 hMSCs (100,000 cells/well) were plated in 6-well culture plates, or 3D pellets were formed by centrifuging 2M hMSCs in 15 mL conical tubes. Monolayered (2D) cells or 3D cell pellets were treated by 1) 100 ng/mL CTGF for 2 wks followed by 10 ng/mL TGFβ3 (C–T), 2) 10 ng/mL TGFβ3 for 2 wks followed by 100 ng/mL CTGF for 2 wks (T-C), 3) mixture of 100 ng/mL CTGF and 10 ng/mL TGFβ3 for 4 wks, or 4) CTGF for 4 wks (C4), TGFβ3 for 4 wks (T4) and growth medium as controls. Fibroblastic induction supplement (FIS) (50 µg/mL ascorbic acids) and chondrogenic induction supplements (CIS) (1% 1×ITS+1 solution, 100 µg/ml sodium pyruvate, 50 µg/ml L-ascorbic Acid 2-phosphate, 40 µg/ml L-proline, 0.1 µM dexamethasone) were included in the CTGF and TGFβ3 treatment, respectively.

Analysis of fibrochondrogenic differentiation: Upon 4 wks of treatments, harvested samples (monolayers and pellet sections) were stained with Alcian blue (AB) and Picrosirious red (PR). GAGs and COL were quantitatively assayed (Biocolor, UK) and normalized to DNA contents. Immunofluorescence was performed to identify cells expressing proCOL-I and/or proCOL-IIα. Briefly, samples were fixed in 10% formalin and washed with 0.1% Triton-X, followed by incubation with rat monoclonal antibody of proCOL-1 (ab64409) (Abcam, Cambridge, Mass.) and mouse monoclonal antibody of proCOL-IIα (ab17717) (Abcam, Cambridge, Mass.) for 1.5 hrs at room temperature. Upon 1 hr incubation with the secondary antibodies (Alexa Fluor®) (Invitrogen, Carlsbad, Calif.) and washing with 0.1% Tween-20 (Sigma, St. Louis, Mo.) solution, samples were examined using a fluorescence microscope (Leica Microsystem, Bannockburn, Ill.).

Results showed that C–T and C+T groups generated notable fibrocartilaginous matrix, positively stained by AB and PR (see e.g., FIG. 1H, J, N, P).

Figure 2:
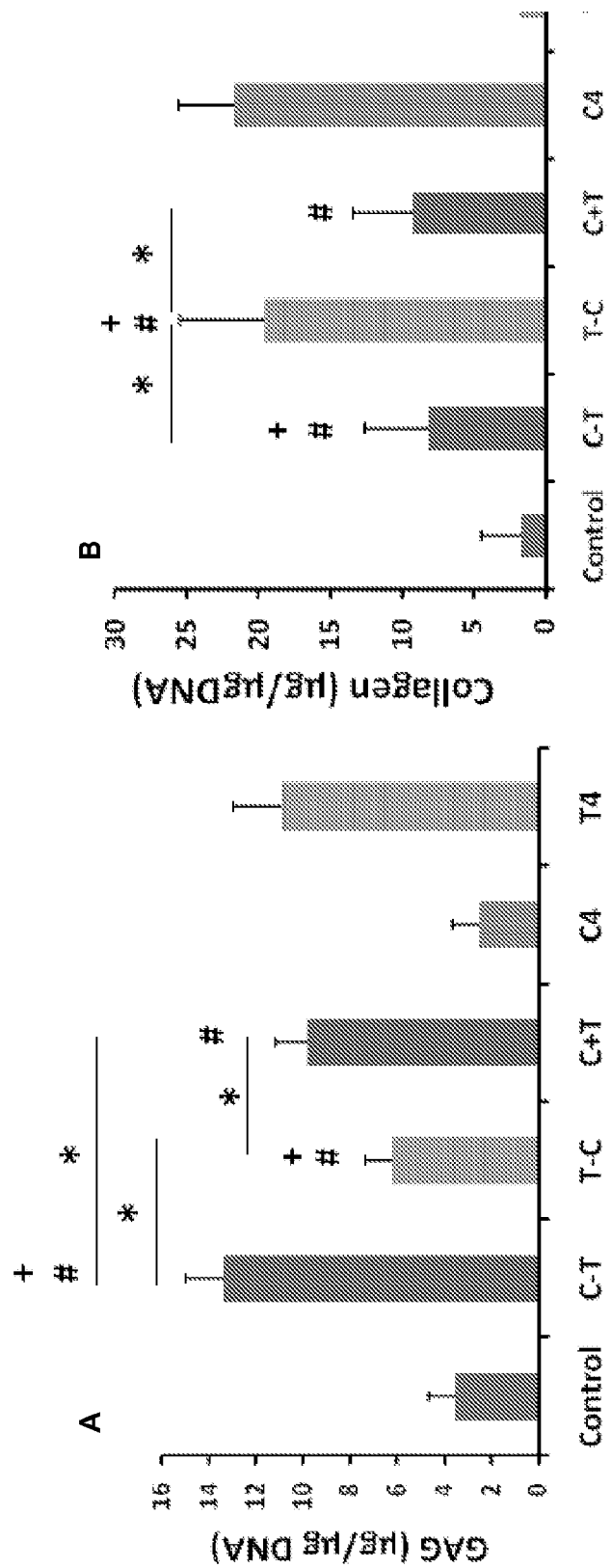
FIG. 2 is a pair of bar graphs showing quantification of GAG (FIG. 2A) and collagen (FIG. 2B) from 2D hMSCs by 4 wks. (n=5 per group; *: $p<0.05$; #: significantly different from control; +: different from positive control).

GAGs amount in C–T was significantly higher than T-C, C+T and control (see e.g., FIG. 2A). C+T group showed significantly more GAGs than T-C and control (see e.g., FIG. 2A). COL amount was significantly higher in T-C group than C–T, C+T and control (see e.g., FIG. 2B). In addition, C–T and C+T showed significant increases in COL as compared to control (see e.g., FIG. 2B).

Figure 3:
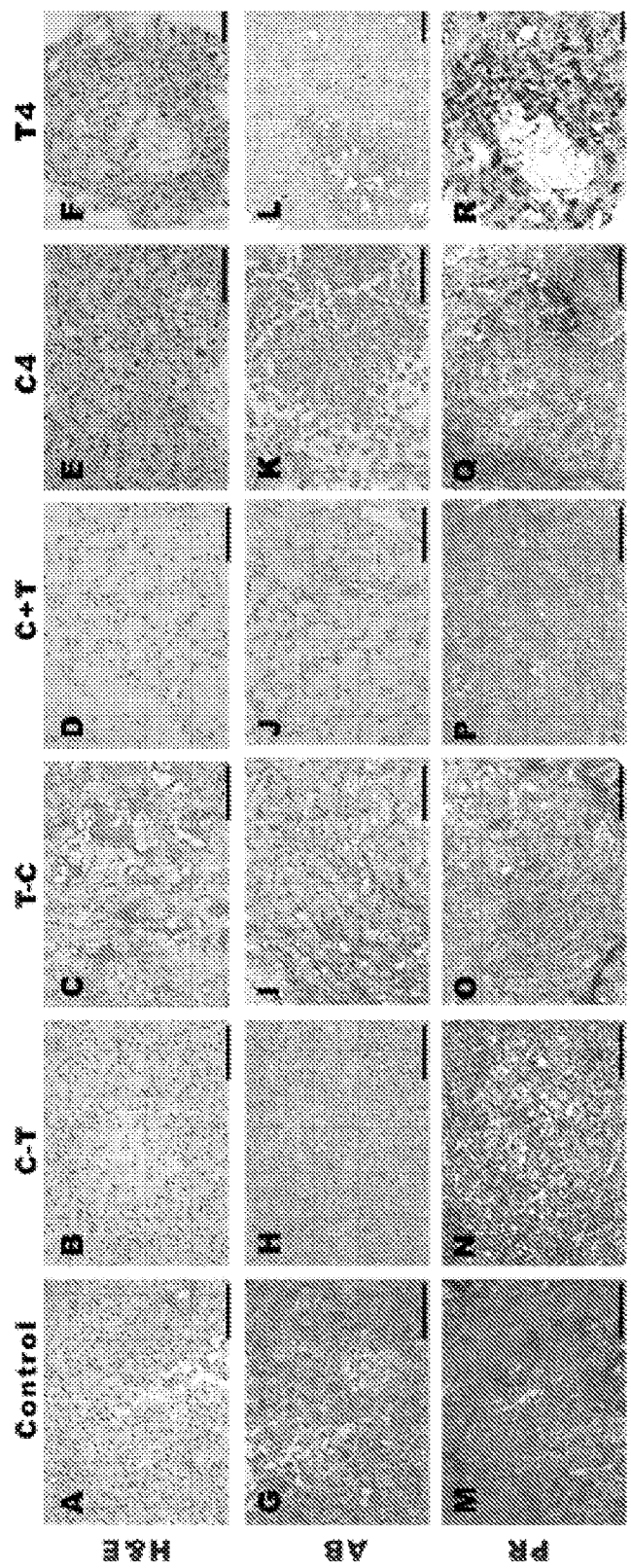
FIG. 3 is a series of images showing fibrochondrogenic differentiation of hMSCs in 3D pellet by 4 wks. Sections were stained with H&E (A-F), AB (G-L) and PR (M-R) (scales: 200 µm). Additional information regarding methodology is provided in Example 1.

In 3D, C–T and C+T groups generated notable fibrocartilaginous matrix, positively stained by AB and PR (see e.g., FIG. 3H, J, N, P). Interestingly, T-C group showed abundant COL deposition (see e.g., FIG. 3O) but limited PG deposition (see e.g., FIG. 3J). Positive controls, C4 and T4, showed only COL or PG, respectively (see e.g., FIG. 3Q, L).

Figure 4:
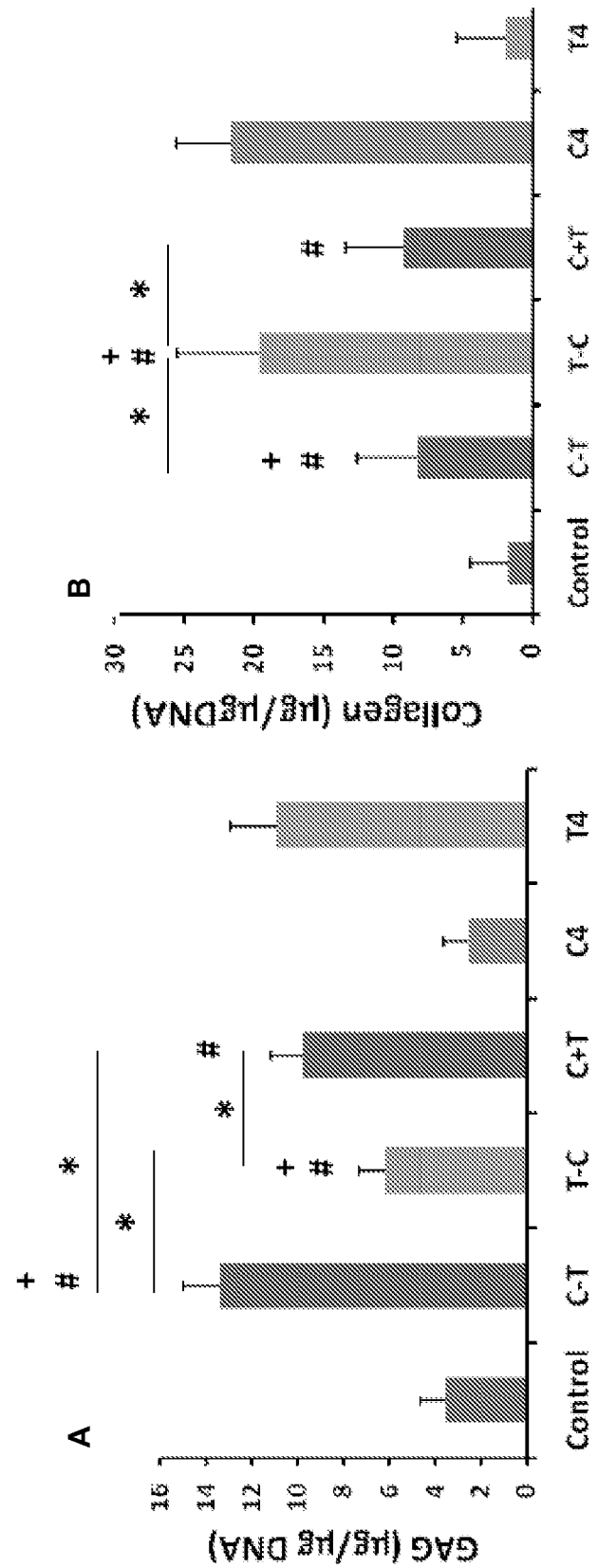
FIG. 4 is a pair of bar graphs showing quantification of GAG (FIG. 4A) and collagen (FIG. 4B) from 3D hMSCs pellet by 4 wks (n=5 per group; *: $p<0.05$; #: significantly different from control; +: different from positive control). Additional information regarding methodology is provided in Example 1.

Quantitatively, GAGs amount in C–T was significantly higher than T-C, C+T and control (see e.g., FIG. 4A). C+T group showed significantly more GAGs than T-C and control (see e.g., FIG. 4A). COL amount was significantly higher in T-C group than C–T, C+T and control (see e.g., FIG. 4B). In addition, C–T and C+T showed significant increases in COL as compared to control (see e.g., FIG. 4B).

Figure 5:
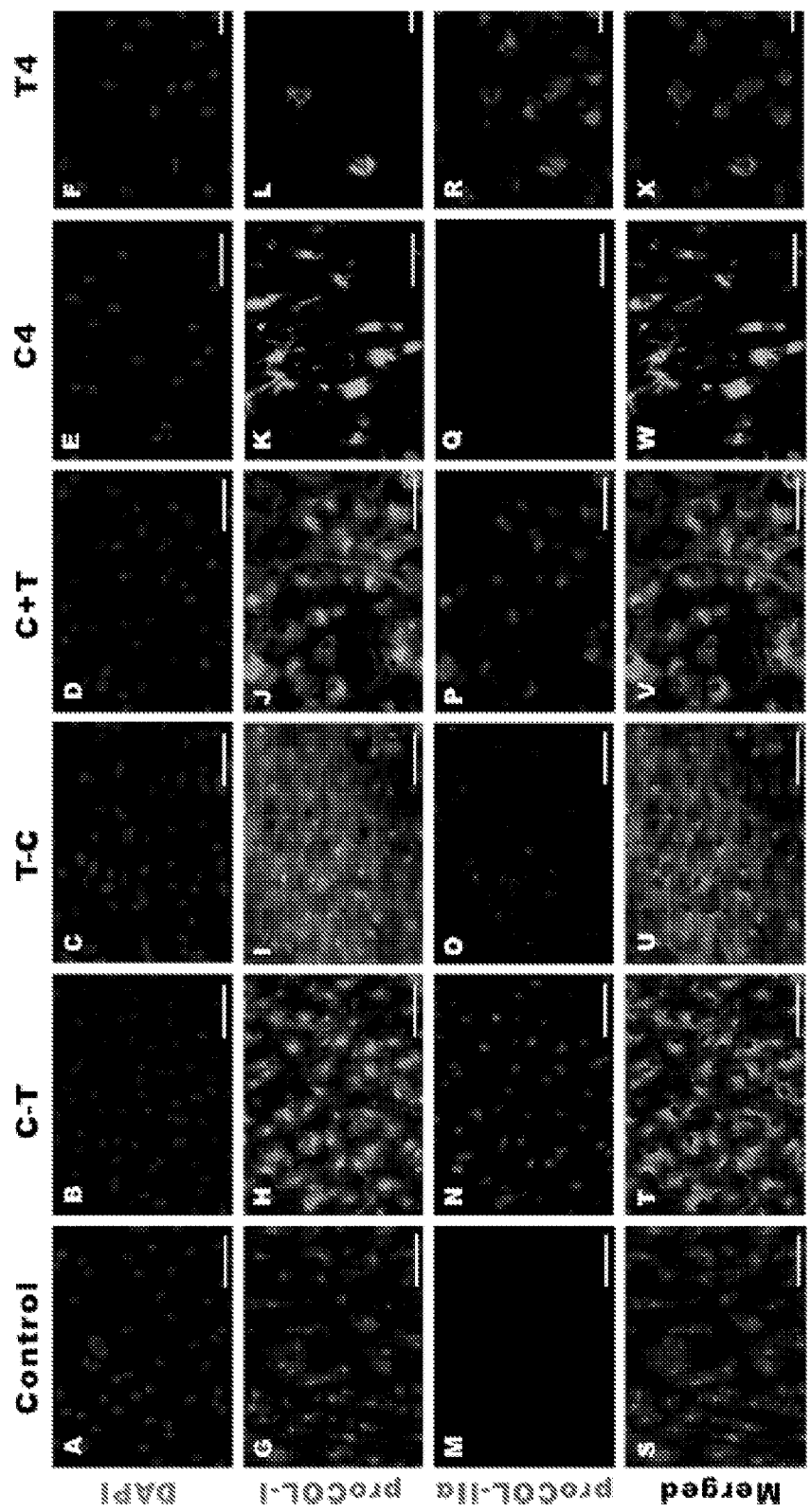
FIG. 5 is a series of images showing immunofluorescence for DAPI (A-F), proCOL-I (G-L) and proCOL-IIα (M-R) by 4 wks. S-X show merged images (scale: 200 µm). Additional information regarding methodology is provided in Example 1.
Figure 6:
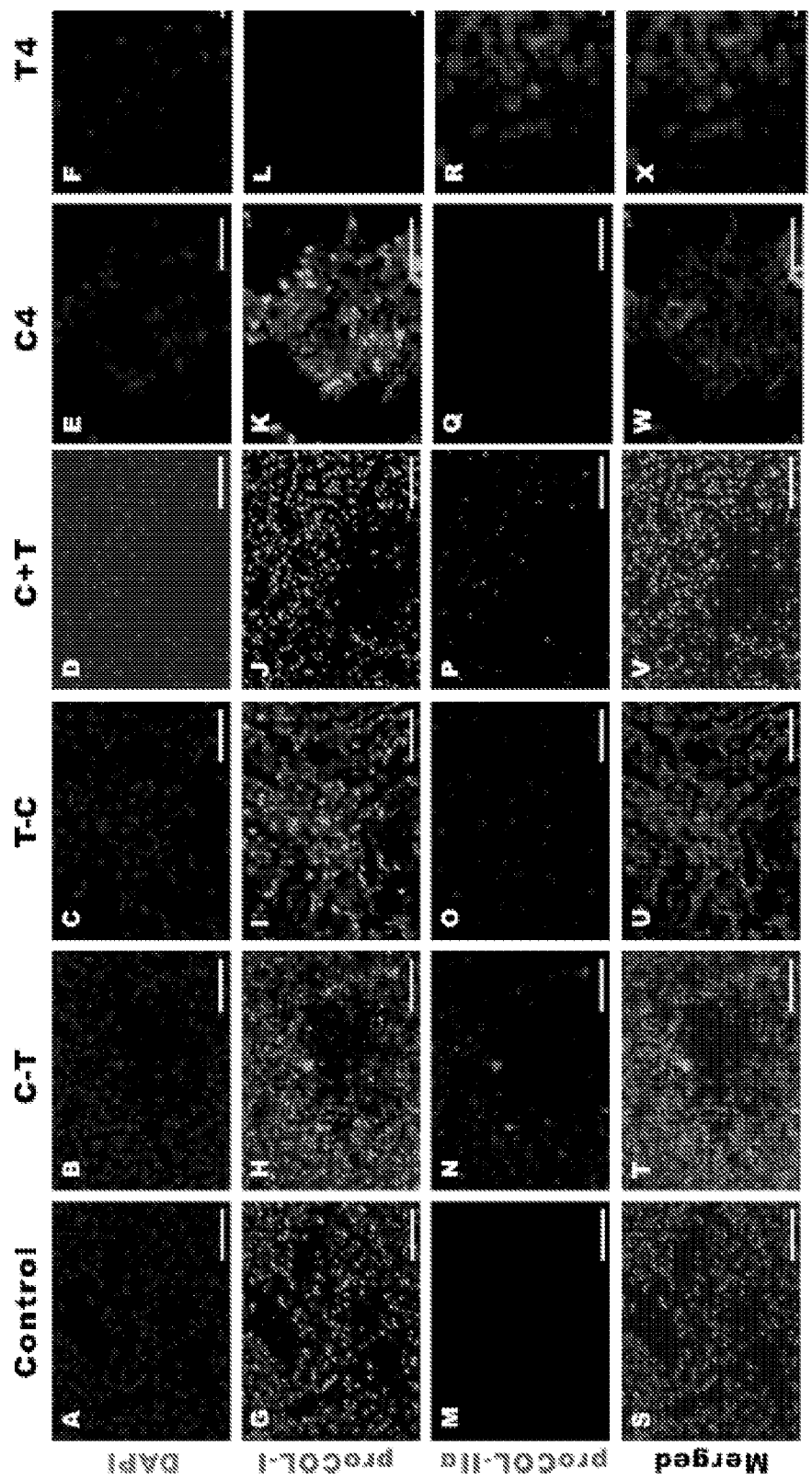
FIG. 6 is a series of images showing immunofluorescence for (4',6-diamidino-2-phenylindole) (DAPI) (FIG. 6A-F), proCOL-I (FIG. 6G-L) and proCOL-IIα (FIG. 6M-R) after 4 wks in 3D. S-X show merged images. (scale: 400 µm).

Immunofluorescence demonstrated that C–T and C+T treatments induced differentiation of hMSCs into proCOL-I+/proCOL-IIα+ fibrochondrocyte-like cells in 2D (see e.g., FIG. 5) and 3D (see e.g., FIG. 6). Cells treated with T-C showed strong expression of proCOL-I but limited expression of proCOL-IIα (see e.g., FIG. 5 in 2D; FIG. 6I, O in 3D). Quantitatively, the number of proCOL-I+/proCOL-IIα+ in C–T treatment (76.9±23%) was significantly higher than in control, T-C, and C+T groups (p<0.05).

Figure 7:
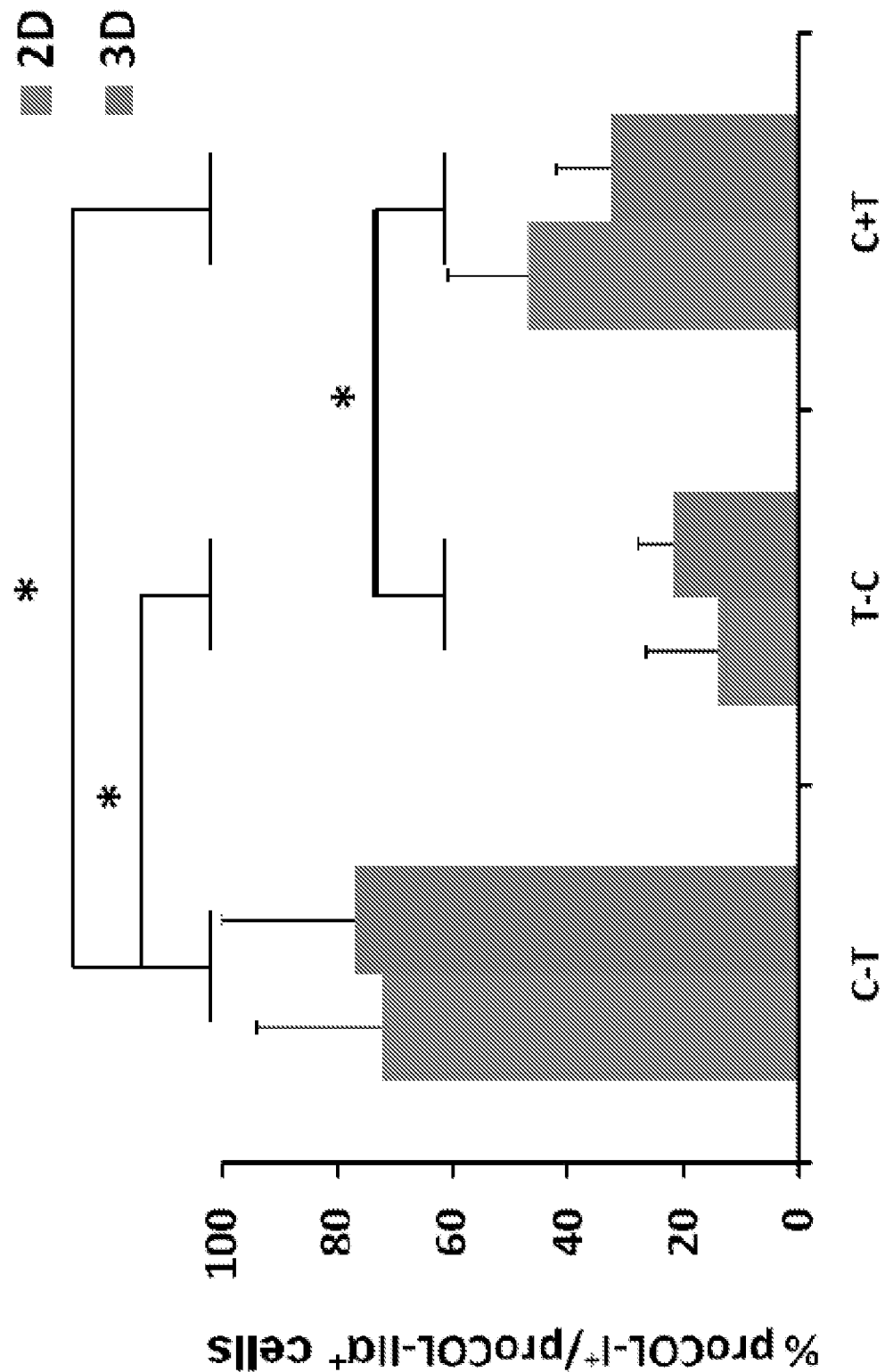
FIG. 7 is a bar graph showing number of proCOL-I+/proCOL-IIα+ cells in C–T, T-C, and C+T treatment after 4 wks in 2D and 3D (n=5; *: $p<0.05$).
Figure 8A:
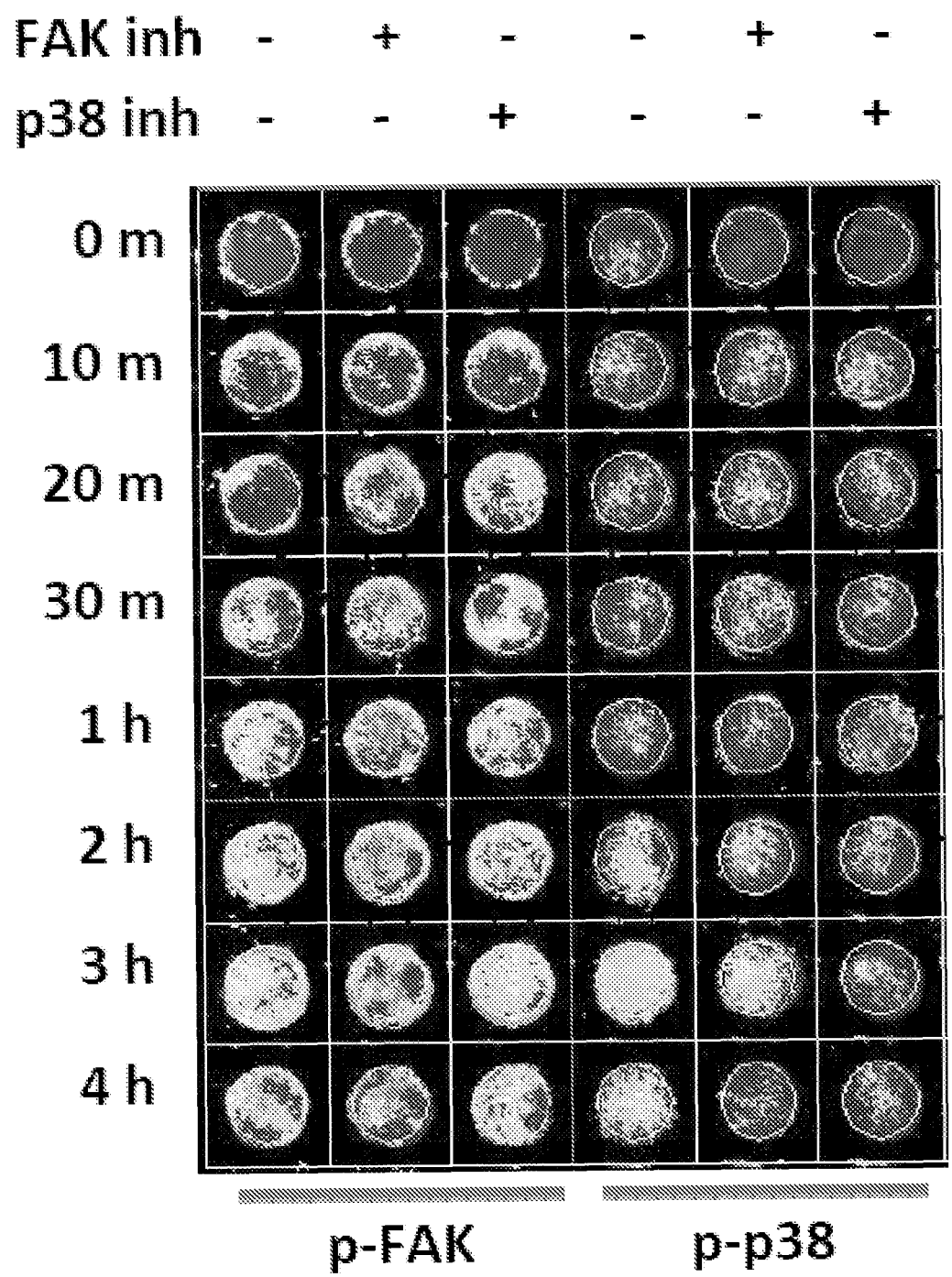
FIG. 8A is an image of in-cell Western for Focal adhesion kinase (FAK) inh (+ or –) and p38 inh (+ or –) over time from 0 minutes to 4 hours.
Figure 9A:
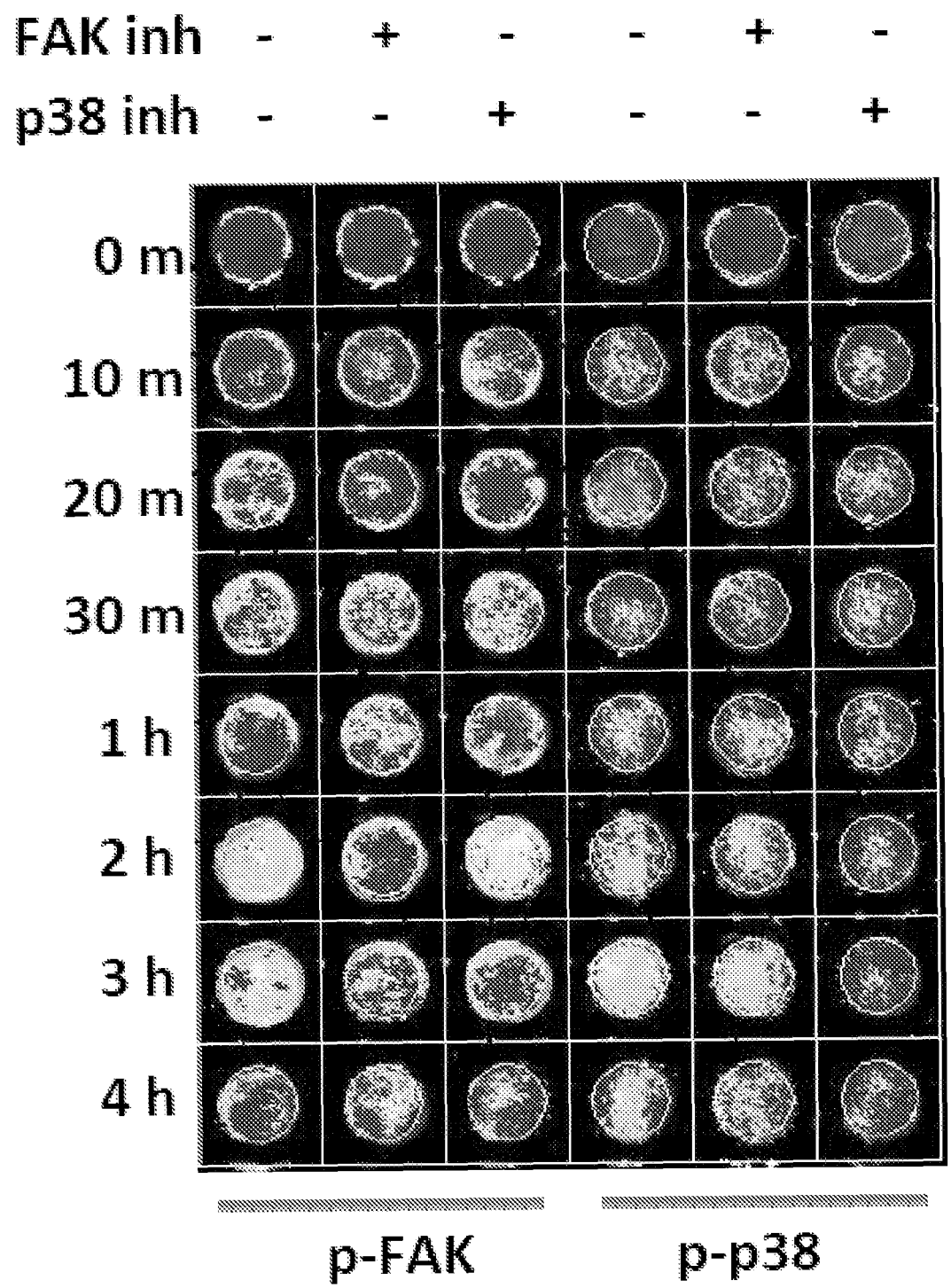
FIG. 9A is an image of in-cell Western for FAK inh (+ or –) and p38 inh (+ or –) over time from 0 minutes to 4 hours.
Figure 10:
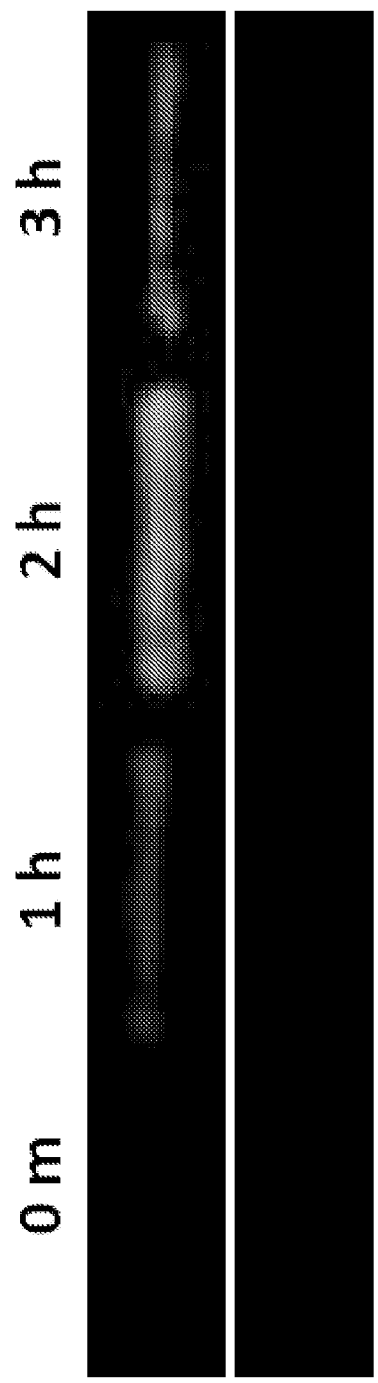
FIG. 10 is an image showing a conventional Western blot (p-FAK): +CTGF treatment.
Figure 11:
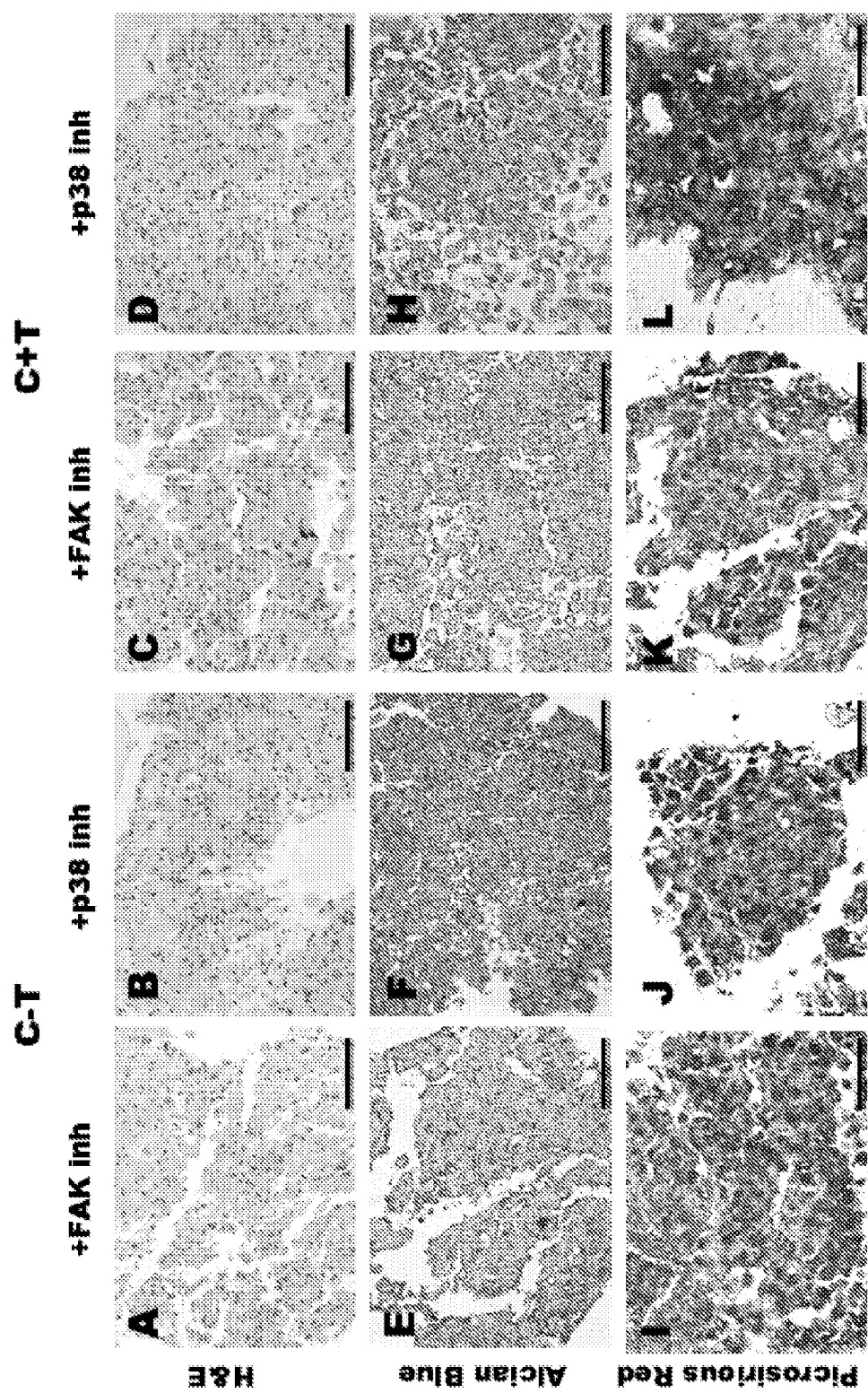
FIG. 11 is a series of tissue stained images of tissue in 3D plus inhibitors +FAKinh and +p38inh for C–T and C+T treatments. Sections were stained with H&E (FIG. 11A-F), AB (FIG. 11 G-L) and PR (FIG. 11M-R) (scales: 200 µm).
Figure 12A:
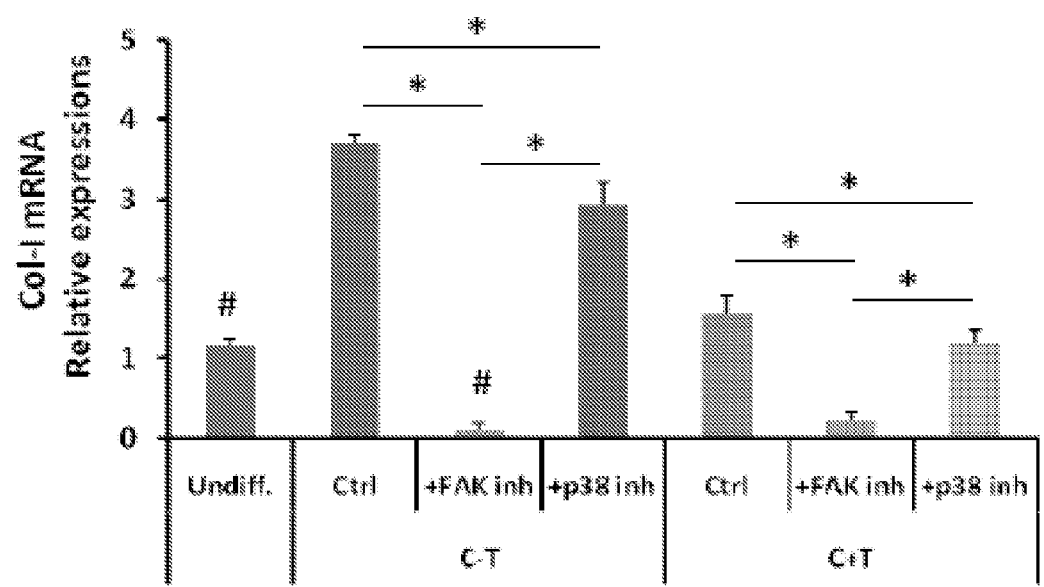
FIG. 12A shows Col-I mRNA expression for C–T and C+T treatments with +FAKinh and +p38inh.
Figure 12B:
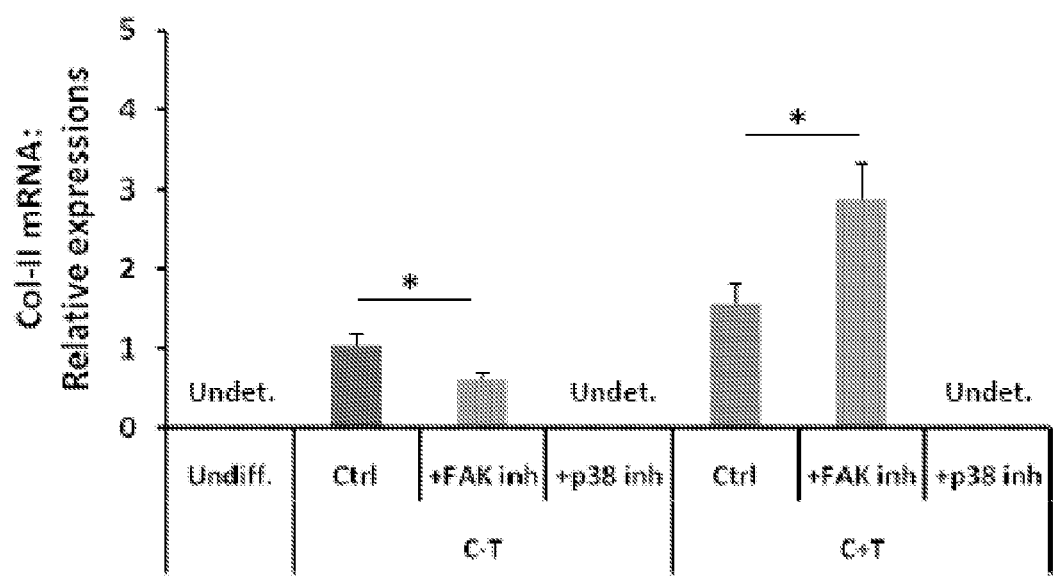
FIG. 12B shows Col-II mRNA expression for C–T and C+T treatments with +FAKinh and +p38inh.
Figure 12C:
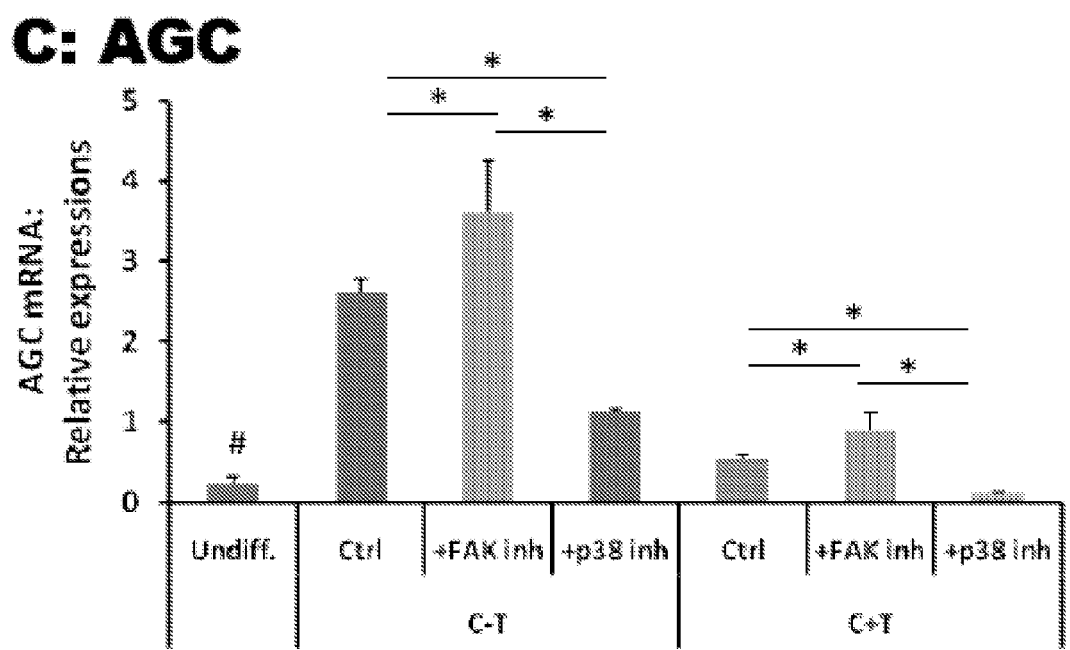
FIG. 12C shows AGC mRNA expression for C–T and C+T treatments with +FAKinh and +p38inh. n=6; *: $p<0.05$; #: significantly different from all other groups.
Figure 15:
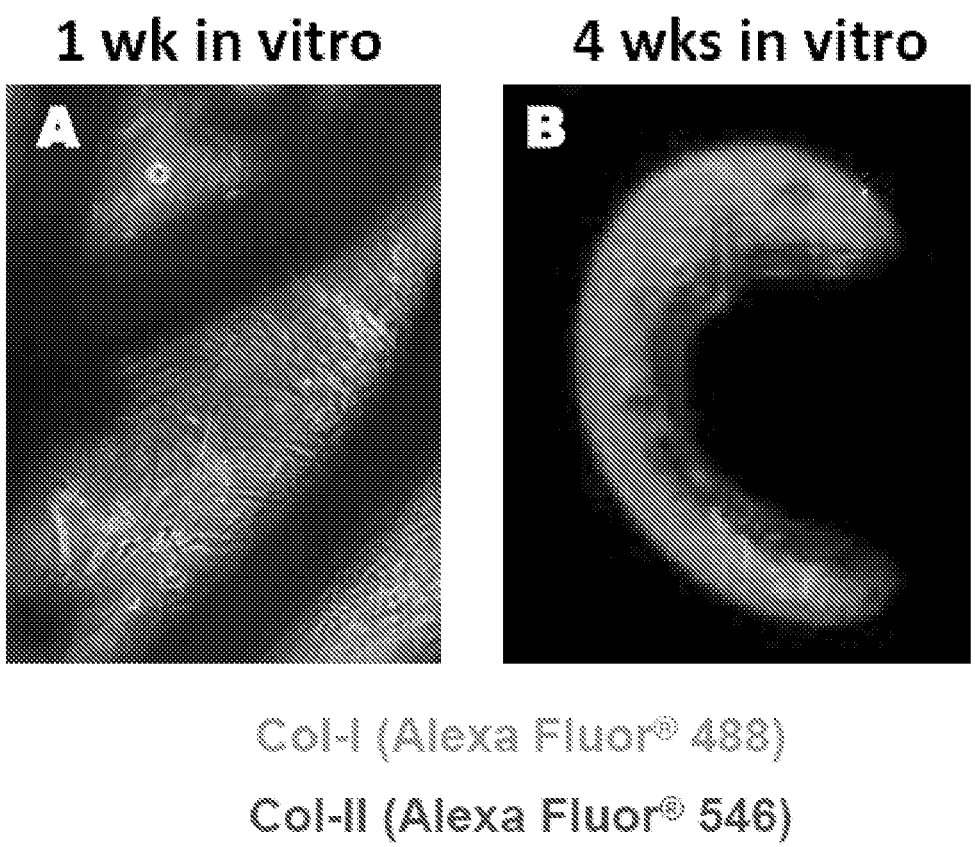
FIG. 15 is a pair of images showing engineered fibrocartilage tissue after 1 week in vitro (FIG. 15A) and after 4 weeks in vitro (FIG. 15B).

In both 2D and 3D, after 4 weeks, there was a significant difference in the ratio of proCOL-I+/proCOL-IIα+ cells in each of C–T, T-C, and C+T treatment (see e.g., FIG. 7). The ratio was highest for C–T and significantly decreased for C+T and further significantly decreased for T-C (see e.g., FIG. 7).

The above study demonstrates derivation of fibrochondrocytes from human mesenchymal stem cells. The above finding that there is a difference in concurrent or step-wise induction of fibrochondrocytes by CTGF and TGFβ3 represents a novel discovery. The derived fibrochondrocytes from the study above simultaneously synthesized both collagen type I and II. sequential CTGF and TGFβ3 applications more readily induced fibrocartilaginous differentiation than concurrent applications of the two factors. It has been reported that CTGF-mediated fibrogenesis is regulated by a separate signaling pathway from TGFβ3-mediated chondrogenesis (Tuli et al. 2003 J Biol Cem 17(278), 41227-41236).

The findings reported herein have provided for stem cell-based fibrocartilage regeneration in knee meniscus, IVD, TMJ and entheses of ligaments and tendons.

Example 2

The following example shows that multiphase knee meniscus was regenerated in an anatomically correct implant with incorporation of CTGF/TGFβ3-µS.

Upon partial meniscectomy in skeletally mature sheep, anatomically correct scaffolds with spatiotemporal delivery CTGF/TGFβ3-βS were implanted. Upon harvest at 2-months post-implantation, H&E staining confirmed cell and tissue ingrowth in the implanted scaffolds (see e.g., FIG. 16 A-C) and cell and tissue integration with host tissue (see e.g., FIG. 16 A). Picrosiriuos Red (PR) staining (see e.g., FIG. 16D-F) revealed collagen-rich matrix in the de novo tissues with more organized collagen structure in outer region (see e.g., FIG. 16D), which is reminiscent of native meniscus. Alcian Blue (AB) staining (see e.g., FIG. 16H-J) demonstrates that the proteoglycan-rich cartilaginous matrix is more dominant toward inner region (see e.g., FIG. 16J), suggesting that the spatiotemporal delivery of CTGF and TGFβ3 leads to native-like multiphase fibrocartilage formation.

Results also showed a partial meniscus replacement at 2 months post-implantation (See e.g., FIG. 17). Multiphase cell phenotypes were found in the regenerated meniscus with spatiotemporal delivery of CTGF and TGFβ3 (see e.g., FIG. 17D-F), which is reminiscent of those of native meniscus (see e.g., FIG. 17A-C). Round chondrocyte-like cells were populated in inner region (see e.g., FIG. 17F), whereas spindle shaped fibroblast-like cells were dominant in outer region (see e.g., FIG. 17D), In middle region, mixed population of fibrochondrocytes were observed (see e.g., FIG. 17E).

The findings reported herein have provided for stem cell-based fibrocartilage regeneration with a partial meniscus replacement using an anatomically correct scaffold implant comprising CTGF/TGFβ3-μS.

What is claimed is:

1. A method of treating a subject having a meniscus tissue defect, the method comprising:
   (a) implanting into a subject in need thereof, at a site of a meniscus tissue defect, a scaffold comprising
      (i) an anatomically correct model of a meniscus,
      (ii) connective tissue growth factor (CTGF) encapsulated in a first microsphere in an outer region of the scaffold, and
      (iii) transforming growth factor β3 (TGFβ3) encapsulated in a second microsphere in an inner region of the scaffold;
   (b) inducing migration of a progenitor cell into or onto the scaffold;
   (c) forming chondrocytes or chondrocyte-like cells in the inner region of the meniscus shaped scaffold; and
   (d) forming fibroblasts or fibroblast-like cells in the outer region of the meniscus shaped scaffold,
   wherein
      the first microsphere releases CTGF before the second microsphere releases TGFβ3, and
      the scaffold does not comprise a transplanted cell prior to implant.

2. The method of claim 1, wherein the scaffold comprises a biocompatible matrix material.

3. The method of claim 1, wherein the scaffold comprises poly(lactic-co-glycolic acid) (PLGA) or polycaprolactone (PCL).

4. The method of claim 1, wherein the scaffold comprises at least one physical channel.

5. The method of claim 1, wherein the scaffold is an anatomically correct model of a knee meniscus.

6. The method of claim 1, wherein the scaffold further comprises:
   a fibroblastic induction supplement comprising ascorbic acid; or
   a chondrogenic induction supplement comprising one or more of ITS+1 solution, sodium pyruvate, ascorbic acid 2-phosphate, proline, or dexamethasone.

7. The method of claim 1, wherein CTGF has a concentration of about 10 to about 1000 ng/mL; and TGFβ3 has a concentration of about 1 to about 1000 ng/mL.

8. The method of claim 1, wherein CTGF has a concentration of about 100 ng/mL; and TGFβ3 has a concentration of about 10 ng/mL.

9. The method of claim 1, wherein the first microsphere is a 50:50 poly(lactic-co-glycolic acid) (PLGA) microsphere and the second microsphere is a 75:25 PLGA microsphere.

10. The method of claim 1, wherein the number of formed fibrochondrocytes or fibrochondrocyte-like cells in the scaffold is at least about 100% greater than the number of fibrochondrocytes or fibrochondrocyte-like cells formed under conditions not comprising CTGF and TGFβ3.

11. The method of claim 1, wherein the fibrochondrocytes or fibrochondrocyte-like cells display one or more of: increased collagen (COL) deposition; increased proteoglycan (PG) deposition; increased glycosaminoglycan (GAG) deposition; increased proCOL-I+; or increased proCOL-IIα+, as compared to the progenitor cell.

12. The method of claim 1, wherein the progenitor cell is a mesenchymal stem cell.

13. The method of claim 1, wherein the progenitor cell is a human mesenchymal stem cell.

14. The method of claim 1, wherein the first microsphere releases CTGF faster than the second microsphere releases TGFβ3.

\* \* \* \* \*

UNITED STATES PATENT AND TRADEMARK OFFICE
CERTIFICATE OF CORRECTION

PATENT NO. : 9,487,754 B2
APPLICATION NO. : 13/877260
DATED : November 8, 2016
INVENTOR(S) : Jeremy J. Mao et al.

It is certified that error appears in the above-identified patent and that said Letters Patent is hereby corrected as shown below:

In the Specification

Column 1, Lines 19-21 should read:
-- This invention was made with government support under grant DE018248 awarded by the National Institutes of Health. The government has certain rights in this invention. --

Signed and Sealed this
Seventh Day of November, 2017

Joseph Matal
*Performing the Functions and Duties of the
Under Secretary of Commerce for Intellectual Property and
Director of the United States Patent and Trademark Office*